United States Patent
Johnson et al.

(10) Patent No.: US 9,399,652 B2
(45) Date of Patent: Jul. 26, 2016

(54) SYNTHETIC ROUTE TO PACTAMYCIN AND PACTAMYCIN ANALOGS

(71) Applicant: The University of North Carolina at Chapel Hill, Chapel Hill, NC (US)

(72) Inventors: Jeffrey Johnson, Carrboro, NC (US); Justin Malinowski, Durham, NC (US); Robert Sharpe, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 14/758,110

(22) PCT Filed: Jan. 23, 2014

(86) PCT No.: PCT/US2014/012685
§ 371 (c)(1),
(2) Date: Jun. 26, 2015

(87) PCT Pub. No.: WO2014/116792
PCT Pub. Date: Jul. 31, 2014

(65) Prior Publication Data
US 2015/0329570 A1    Nov. 19, 2015

Related U.S. Application Data

(60) Provisional application No. 61/756,113, filed on Jan. 24, 2013.

(51) Int. Cl.
| | | |
|---|---|---|
| C07F 7/10 | (2006.01) |
| C07F 7/18 | (2006.01) |
| C07C 275/24 | (2006.01) |
| C07C 275/26 | (2006.01) |

(52) U.S. Cl.
CPC ............. *C07F 7/1804* (2013.01); *C07C 275/24* (2013.01); *C07C 275/26* (2013.01); *C07F 7/1848* (2013.01); *C07B 2200/07* (2013.01); *C07C 2101/08* (2013.01)

(58) Field of Classification Search
CPC .......................................................... C07F 7/18
USPC .......................................................... 556/420
See application file for complete search history.

(56) References Cited

FOREIGN PATENT DOCUMENTS

WO    WO 2008/131258 A2    10/2008

OTHER PUBLICATIONS

Malinowski et al., Organic Letters (2012), 14(11), 2878-2881.*
International Search Report and Written Opinion, PCT/US2014/012685, mailed Apr. 8, 2015.
Hamashima Y et al. $Pd^{II}$-catalyzed asymmetric addition reactions of 1,3-dicarbonyl compounds: Mannish-type reactions with N-Boc imines and three-component aminomethylation. Chemistry an Asian Journal. 2008; 3: 1443-1455.
Hanessian S et al. Total synthesis of pactamycin. Angewandte Chemie International Edition, 2011; 50: 3497-3500.
Hanessian S et al. Total synthesis of pactamycin and pactamycate: a detailed account. Journal of Organic Chemistry. 2012; 77: 9458-9472.

* cited by examiner

*Primary Examiner* — Porfirio Nazario Gonzalez
*Assistant Examiner* — Kofi Adzamli
(74) *Attorney, Agent, or Firm* — Myers Bigel & Sibley, P.A.

(57) ABSTRACT

Methods and intermediates useful for making compounds of Formula (I) are described, including a general method of making an alpha, beta-diamino ketone by reacting an imine with a 2-amino-substituted 1,3-dicarbonyl in a Mannich addition reaction to produce said alpha,beta-diamino ketone.

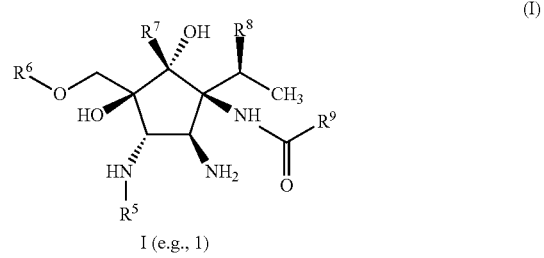

I (e.g., 1)

3 Claims, No Drawings

SYNTHETIC ROUTE TO PACTAMYCIN AND PACTAMYCIN ANALOGS

RELATED APPLICATIONS

This application is a 35 U.S.C. §371 national phase entry of PCT Application PCT/US2014/012685, filed Jan. 23, 2014, and published in English on Jul. 31, 2014, as International Publication No. WO 2014/116792, and which claims the benefit of U.S. Provisional Application No. 61/756,113, filed Jan. 24, 2013, the disclosure of each of which is incorporated herein by reference in its entirety.

GOVERNMENT SUPPORT

This invention was made with US Government support under Grant No. GM084927 from the National Institutes of Health. The US Government has certain rights to this invention.

FIELD OF THE INVENTION

The present invention concerns methods and intermediates for making pactamycin and analogs thereof, along with compounds, compositions and methods of using the same.

BACKGROUND OF THE INVENTION

Pactamycin and certain analogs thereof are known and described in, for example, S. Hannasian et al., *J. Org. Chem.* 77, 9458-9472 (2012); W. Lu et al., *Chemistry and Biology* 18, 425-431 (2011), and T. Mahmud, PCT Publication No. WO2012/018854. Some prior syntheses of these compounds rely on enzymatic mechanisms, which, among other things, limits the substitutions which can be obtained thereon. Other synthetic sequences are lengthy, which limit the analogs that can be created. Accordingly, there is a need for new ways to make pactamycin and analogs thereof which do not rely on enzymatic steps or long synthetic sequences.

SUMMARY OF THE INVENTION

A first aspect of the present invention is compounds of Formula I and methods of making the same:

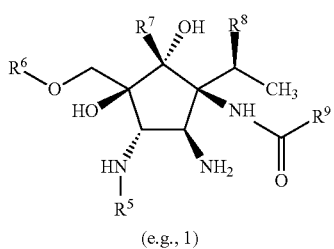

(e.g., 1)

wherein:
R$^5$ is H, alkyl, aryl or heteroaryl;
R$^6$ is H or —R$^a$R$^b$, where R$^a$ is alkyl or carbonyl, and R$^b$ is alkyl, aryl, or heteroaryl;
R$^7$ is H, alkyl, aryl, or heteroaryl;
R$^8$ is H, hydroxy, silyloxy, acyloxy, or alkoxy; and
R$^9$ is —N(R$^c$R$^d$), —OR$^c$, or —SR$^c$, where R$^c$ and R$^d$ are each independently selected alkyl, aryl, or heteroaryl, or R$^c$ and R$^d$ together form an alkylene bridge;

A second aspect of the present invention is pharmaceutical formulations comprising certain subgroups of compounds of Formula I or Formula II (below) (e.g., excluding pactamycin, pactamycate, and those analogs described in PCT Publication No. WO2012/018854), including pharmaceutically acceptable salts thereof.

A further aspect of the present invention is methods of treating, and compounds of Formula I or Formula II (below) for use in treating, disorders and diseases such as (for example) malaria, bacterial and viral infections, tumors and cancers.

A still further aspect of the invention is intermediates useful for making compounds of Formula I above, and methods of making such intermediates.

In contrast to prior enzymatic and synthetic methods, the present invention includes a method of making an early intermediate for the synthesis of compounds of Formula I by a Mannich addition of 2-amino-substituted 1,3-dicarbonyls. While Mannich reactions on other reactants are known (see, e.g., S. Lou et al., *J. Am. Chem. Soc.* 127, 11256 (2005); A Ting et al., *Org. Lett.* 8, 2003 (2006); S. Lou et al., *J. Am. Chem. Soc* 129, 15398 (2007)), Mannich additions of 2-amino substituted 1,3-dicarbonyls have not heretofore been suggested or described. Hence the present invention generally provides a method of making an alpha,beta-diamino ketone, comprising: reacting an imine with a 2-amino-substituted 1,3-dicarbonyl in a Mannich addition reaction to produce said alpha,beta-diamino ketone. The method is useful for making the compounds described herein, or others.

The foregoing and other objects and aspects of the invention are explained in greater detail in the drawings herein and the specification set forth below.

DETAILED DESCRIPTION OF THE PREFERRED EMBODIMENTS

1. Definitions

"Alkyl" as used herein alone or as part of another group, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "alkyl" or "loweralkyl" is intended to include both substituted and unsubstituted alkyl or loweralkyl unless otherwise indicated and these groups may be substituted with groups selected from halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkenyl" as used herein alone or as part of another group, refers to a straight or branched chain hydrocarbon containing from 1 to 10 carbon atoms (or in loweralkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkynyl" as used herein alone or as part of another group, refers to a straight or branched chain hydrocarbon containing from 1 to 10 carbon atoms (or in loweralkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralkynyl unless otherwise indicated and these groups may be substituted with the same groups as set forth in connection with alkyl and loweralkyl above.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclobutyl. These rings may be optionally substituted with additional substituents as described herein such as halo or loweralkyl. The term "cycloalkyl" is generic and intended to include heterocyclic groups as discussed below unless specified otherwise.

"Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system, Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Heteroaryl" as used herein is as described in connection with heterocyclo above.

"Alkoxy" as used herein alone or as part of another group, refers to an alkyl or loweralkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Halo" as used herein refers to any suitable halogen, including —F, —Cl, —Br, and —I.

"Mercapto" as used herein refers to an —SH group.

"Azido" as used herein refers to an —N$_3$ group.

"Cyano" as used herein refers to a —CN group.

"Formyl" as used herein refers to a —C(O)H group.

"Carboxylic acid" as used herein refers to a —C(O)OH group.

"Hydroxyl" as used herein refers to an —OH group.

"Nitro" as used herein refers to an —NO$_2$ group.

"Acyl" as used herein alone or as part of another group refers to a —C(O)R radical, where R is any suitable substituent such as aryl, alkyl, alkenyl, alkynyl, cycloalkyl or other suitable substituent as described herein.

"Alkylthio" as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Amino" as used herein means the radical —NH$_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —NR$_a$R$_b$, where R$_a$ and R$_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical —NR$_a$R$_b$, where R$_a$ is an acyl group as defined herein and R$_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Amide" as used herein alone or as part of another group refers to a —C(O)NR$_a$R$_b$ radical, where R$_a$ and R$_b$ are any suitable substituent such as alkyl, cycloalkyl, alkenyl, alkynyl or aryl.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as amino, alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Sulfonamide" as used herein alone or as part of another group refers to a —S(O)$_2$NR$_a$R$_b$ radical, where R$_a$ and R$_b$ are any suitable substituent such as H, alkyl, cycloalkyl, alkenyl, alkynyl or aryl.

"Urea" as used herein alone or as part of another group refers to an —N(ROC(O)NR$_a$R$_b$ radical, where R$_a$, R$_b$ and R$_c$ are any suitable substituent such as H, alkyl, cycloalkyl, alkenyl, alkynyl or aryl.

"Alkoxyacylamino" as used herein alone or as part of another group refers to an —N(R$_a$)C(O)OR$_b$ radical, where R$_a$, R$_b$ are any suitable substituent such as H, alkyl, cycloalkyl, alkenyl, alkynyl or aryl.

"Aminoacyloxy" as used herein alone or as part of another group refers to an —OC(O)NR$_a$R$_b$ radical, where R$_a$ and R$_b$ are any suitable substituent such as H, alkyl, cycloalkyl, alkenyl, alkynyl or aryl.

"Polar group" as used herein refers to a group wherein the nuclei of the atoms covalently bound to each other to form the group do not share the electrons of the covalent bond(s) joining them equally; that is the electron cloud is denser about one atom than another. This results in one end of the covalent bond(s) being relatively negative and the other end relatively positive; i.e., there is a negative pole and a positive pole. Examples of polar groups include, without limitations, halo, hydroxy, alkoxy, carboxy, nitro, cyano, amino (primary, secondary and tertiary), amido, ureido, sulfonamido, sulfinyl, sulfhydryl, silyl, S-sulfonamido, N-sulfonamido, C-carboxy, O-carboxy, C-amido, N-amido, sulfonyl, N-tert-butoxycarbonyl (or "t-BOC") groups, phosphoric), morpholino, piperazinyl, tetrazolo, and the like. See, e.g., U.S. Pat. No. 6,878,733, as well as alcohol, thiol, polyethylene glycol, polyol (including sugar, aminosugar, uronic acid), sulfonamide, carboxamide, hydrazide, N-hydroxycarboxamide, urea, metal chelates (including macrocyclic ligand or crown ether metal chelates). The polar group can be an ionic group.

"Ionic group" as used herein includes anionic and cationic groups, and includes groups (sometimes referred to as "ionogenic" groups) that are uncharged in one form but can be easily converted to ionic groups (for example, by protonation or deprotonation in aqueous solution). Examples include but are not limited to carboxylate, sulfonate, phosphate, amine, N-oxide, and ammonium (including quaternized heterocyclic amines such as imidazolium and pyridinium) groups. See, e.g., U.S. Pat. Nos. 6,478,863; 6,800,276; and 6,896,246. Additional examples include uronic acids, carboxylic acid, sulfonic acid, amine, and moieties such as guanidinium, phosphoric acid, phosphonic acid, phosphatidyl choline, phosphonium, borate, sulfate, etc.

"Deuterium" as used herein alone or as part of another group, refers to a safe, non-radioactive relative of hydrogen. Any hydrogen in a group or substituent described above may be replaced with deuterium to provide a "deuterated" compound, in some embodiments to modify and/or improve metabolic stability, resulting in better safety, tolerability and/or efficacy.

"Linking group" as used herein are generally bivalent aromatic, aliphatic, or mixed aromatic and aliphatic groups. Thus linking groups include linear or branched, substituted or unsubstituted aryl, alkyl, alkylaryl, or alkylarylalkyl linking groups, where the alkyl groups are saturated or unsaturated, and where the alkyl and aryl groups optionally containing independently selected heteroatoms such as 1, 2, 3 or 4 heteroatoms selected from the group consisting of N, O, and S. In some embodiments, linking groups containing from 2 to 20 carbon atoms are preferred. Numerous examples of suitable linking groups are known, including but not limited to those described in, U.S. Pat. Nos. 8,247,572; 8,097,609; 6,624,317; 6,613,345; 6,596,935; and 6,420,377, the disclosures of which are incorporated by reference herein in their entirety.

"Leaving group" as used herein may be any suitable leaving group. Numerous alternatives are known to those skilled in the art. See, e.g., U.S. Pat. Nos. 8,338,586 and 8,338,620. Examples include, but are not limited to, $X^1$ is —OCH$_2$CN, halo, fluoride, chloride, bromide, iodide, alkylsulfonyl (such as mesylate, tosylate, benzenesulfonate, triflate), N,N,N',N'-dialkylurea, etc.

"Protecting group" as used herein may be any suitable protecting group. See, e.g., A. Isidro-Llobet et al., Amino Acid-Protecting Groups, *Chem. Rev.* 109, 2455-2504 (2009) and T. Greene and P Wuts, *Protective Groups in Organic Synthesis* (3d Ed. 1999). Non-limiting examples of protecting groups include, but are not limited to: Alkaline-stable amino protecting groups such as: 2-(2-Nitrophenyl)propyloxycarbonyl (NPPOC), Methylenedioxy-6-nitrophenyl)propyloxycarbonyl (MNPPOC), 2-(4-Biphenyl)isopropoxycarbonyl (Bpoc), 2,2,2-Trichloroethyloxycarbonyl (Troc), 2,4-Dinitrobenzenesulfonyl (dNBS), 2-Chlorobenzyloxycarbonyl (Cl-Z), 2-Nitrophenylsulfenyl (Nps), 4-Methyltrityl (Mtt), 9-(4-Bromophenyl)-9-fluorenyl (BrPhF), Allyloxycarbonyl (Alloc), Azidomethoxycarbonyl (Azoc), Benzyloxycarbonyl (Z), o-Nitrobenzyloxycarbonyl (oNZ) and 6-Nitroveratryloxycarbonyl (NVOC), p-Nitrobenzyloxycarbonyl (pNZ), Propargyloxycarbonyl (Poc), tert-Butyloxycarbonyl (Boc), Trityl (Trt), α,α-Dimethyl-3,5-dimethoxybenzyloxycarbonyl (Ddz), and α-Azido Carboxylic Acids, etc. Alkaline-labile amino protecting groups, such as: (1-(4,4-Dimethyl-2,6-dioxocyclohex-1-ylidene)-3-ethyl) (Dde), (1,1-Dioxobenzo[b]thiophene-2-yl)methyloxycarbonyl (Bsmoc), (1,1-Dioxonaphtho[1,2-b]thiophene-2-yl)methyloxycarbonyl (r-Nsmoc), 1-(4,4-Dimethyl-2,6-dioxocyclohex-1-ylidene)-

3-methylbutyl (ivDde), 2-(4-Nitrophenylsulfonyl)ethoxycarbonyl (Nsc), 2-(4-Sulfophenylsulfonyl)ethoxycarbonyl (Sps), 2,7-Di-tert-butyl-Fmoc (Fmoc*), 2-[Phenyl(methyl)sulfonio]ethyloxycarbonyl tetrafluoroborate (Pms), 2-Fluoro-Fmoc (Fmoc(2F)), 2-Monoisooctyl-Fmoc (mio-Fmoc) and 2,7-Diisooctyl-Fmoc (dio-Fmoc), 9-Fluorenylmethoxycarbonyl (Fmoc), Ethanesulfonylethoxycarbonyl (Esc), and Tetrachlorophthaloyl (TCP), Acetyl (Ac), Benzoyl (Bz), Tosyl (Ts), etc. Alkaline-stable carboxylic acid protecting groups, such as: (2-Phenyl-2-trimethylsiylyl)ethyl (PT-MSE), 1,1-Dimethylallyl (Dma), 2-(Trimethylsilyl)isopropyl (Tmsi), 2,2,2-Trichloroethyl (Tce), 2,4-Dimethoxybenzyl (Dmb), 2-Chlorotrityl (2-Cl-Trt), 2-Phenylisopropyl (2-PhiPr), 2-Phenylisopropyl (2-PhiPr), 2-Trimethylsilylethyl (TMSE), 4-(3,6,9-Trioxadecyl)oxybenzyl (TEGBz or TEGBn), 4,5-Dimethoxy-2-nitrobenzyl (Dmnb), 5-Phenyl-3,4-ethylenedioxythenyl Derivatives (Phenyl-EDOTn), Allyl (Al), Benzyl (Bn), Cyclohexyl (cHx), Pentaamine Cobalt (III), Phenacyl (Pac), p-Hydroxyphenacyl (pHP), p-Nitrobenzyl (pNB), tert-Butyl (tBu), β-3-Methylpent-3-yl (Mpe), and β-Menthyl (Men), etc. Alkaline-labile carboxylic acid protecting groups: 9-Fluorenylmethyl (Fm), Methyl (Me) and Ethyl (Et), Carbamoylmethyl (Cam), and 4-(N-[1-(4,4-dimethyl-2,6-dioxocyclohexylidene)-3-methylbutyl]amino)benzyl (Dmab), etc. Additional examples include but are not limited to those set forth in U.S. Pat. Nos. 8,299,279; 8,129,561; 8,008,500; 7,713,927; and 7,521,529, the disclosures of all of which are incorporated herein by reference.

"Organometallic nucleophile" as used herein has its conventional meaning and may be any suitable organometallic nucleophile, including Grigniard reagents, organolithium compounds, and organocerium compounds such as RMgBr, RMgCl, RLi, RLi, RCeCl$_2$, etc., where R is an organic group.

"Treat" as used herein refers to any type of treatment that imparts a benefit to a patient afflicted with a disease, including improvement in the condition of the patient (e.g., in one or more symptoms), delay in the progression of the disease, delay in onset of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

2. Active Compounds and Methods of Making

As noted above, the present invention provides compounds of Formula I:

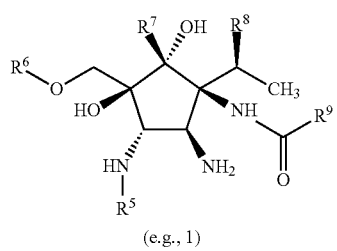

(e.g., 1)

wherein:
$R^5$ is H, alkyl, aryl or heteroaryl;
$R^6$ is H or —$R^aR^b$, where $R^a$ is alkyl or carbonyl, and $R^b$ is alkyl, aryl, or heteroaryl;
$R^7$ is H, alkyl, aryl, or heteroaryl;

$R^8$ is H, hydroxy, silyloxy, acyloxy, or alkoxy; and
$R^9$ is —N($R^cR^d$), —OR$^c$, or —SR$^c$, where $R^c$ and $R^d$ are each independently selected alkyl, aryl, or heteroaryl, or $R^c$ and $R^d$ together form an alkylene bridge.

In some embodiments of the foregoing, $R^5$ is not aryl. In some embodiments of the foregoing, $R^5$ is aryl, but not phenyl (e.g., naphthyl, or other fused ring aryl). In some embodiments of the foregoing, $R^5$ is phenyl, but subject to the proviso that said phenyl is not meta substituted with an acetyl group or a group of the formula is —C(=O)CH$_2$R$^{77}$, where R$^{77}$ is H, hydroxyl, halo, lower aliphatic, or amino. In some embodiments of the foregoing, $R^5$ is a substituent of the formula:

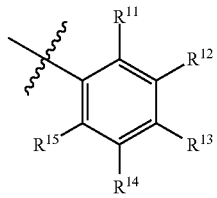

wherein: $R^{11}$, $R^{12}$, $R^{13}$, $R^{14}$, and $R^{15}$ are each independently selected from the group consisting of halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, aryloxy, ester, amide, sulfonamide, urea, alkoxyacylamino, aminoacyloxy, nitro or cyano where m=0, 1, 2 or 3, or other electron withdrawing or electron donating group, subject to the proviso that neither $R^{12}$ nor $R^{14}$ is —C(=O)CH$_2$R$^{77}$, where R$^{77}$ is H, hydroxyl, halo, lower aliphatic, or amino.

Compounds of Formula I can be made by deprotecting a compound of Formula II (16):

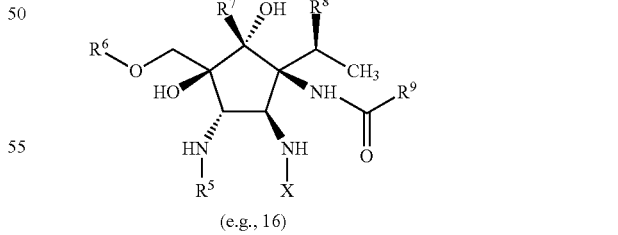

(e.g., 16)

where X is a protecting group to produce said compound of Formula I. Those skilled in the art will appreciate that, in some embodiments, the deprotecting step may be skipped and compounds of Formula II may themselves be used as active compounds, prepared as pharmaceutical salts and formulations as described herein, and used in the methods of treatment as described herein.

Compounds of Formula II: can be made by reacting a compound of Formula III:

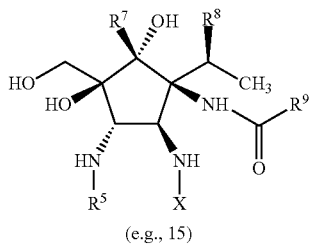

(e.g., 15)

with a compound of Formula IV:

$X^1—R^6$  IV (18)

where $X^1$ is a leaving group and $R^6$ is as given above to produce the compound of Formula II.

Compound of Formula III can be made by deprotecting a compound of Formula V:

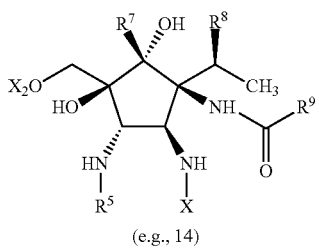

(e.g., 14)

where $X^2$ is a protecting group to produce said compound of Formula III.

Compound of Formula V can be made by reacting a compound of Formula VI:

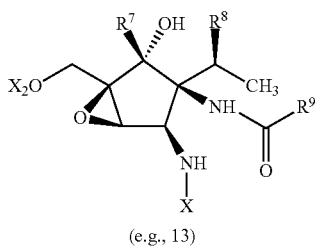

(e.g., 13)

with a compound of Formula VII:

$H_2N—R^5$  VII (e.g., 17)

to produce the compound of Formula V.

Compound of Formula VI can be made by reacting a compound of Formula

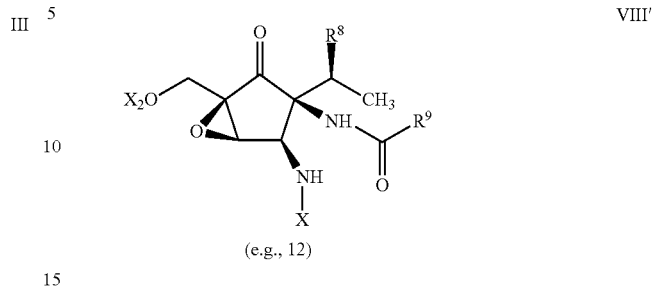

(e.g., 12)

with $R^7M$, where $R^7M$ is an organometallic nucleophile in which $R^7$ is as given above, to produce said compound of Formula VI.

Compounds of Formula VIII' above can be made by reacting a compound of Formula VIII:

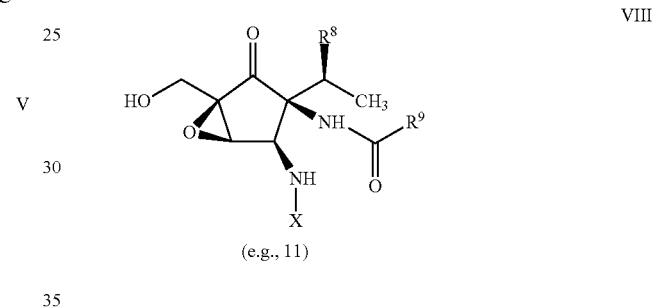

(e.g., 11)

with a compound of the formula $X^2Z$, where $X^2$ is as given above and Z is a leaving group, to produce the compound of Formula VIII'.

Compound of Formula VIII above can be made by epoxidizing a compound of Formula IX:

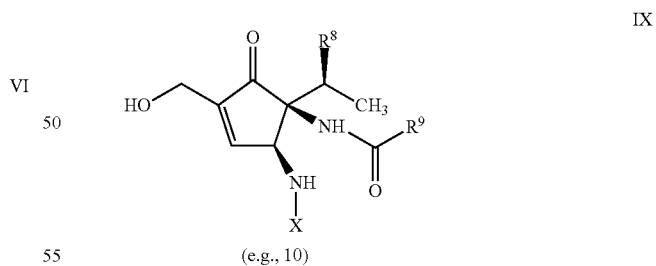

(e.g., 10)

in an epoxidation reaction to produce the compound of Formula VIII. The epoxidation reaction can be carried out in accordance with known techniques, such as by reacting with hydrogen peroxide, tert-butyl hydroperoxide, or m-chloroperoxybenzoic acid (MCPBA) in a suitable solvent (typically a polar organic solvent such as methanol, ethanol, etc), in the presence or absence of a base such as sodium hydroxide.

Compounds of Formula IX above can be made by condensing a compound of Formula X:

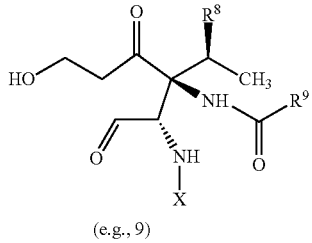

(e.g., 9)

in an aldol condensation reaction to produce the compound of Formula IX.

Compound of Formula X above can be made by reacting a compound of Formula XI:

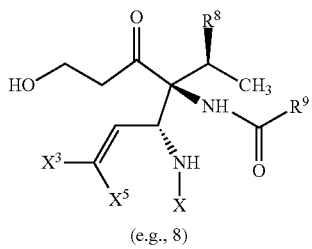

(e.g., 8)

where $X^3$ and $X^5$ are independently selected leaving groups; in an oxidative cleavage reaction to produce the compound of Formula X. Any suitable oxidative cleavage reaction may be employed including but not limited to ozonolysis, or contacting to potassium permanganate or other suitable oxidizing reagent.

Compound of Formula XI above can be made by reacting a compound of Formula XII':

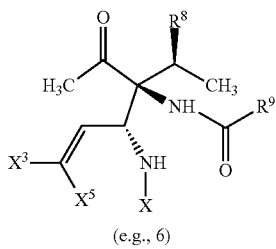

(e.g., 6)

with formaldehyde in an aldol addition to produce said compound of Formula XI.

Compounds of Formula XII' can be made by protecting, etherifying, or deoxygenating the secondary alcohol q in a compound of Formula XII:

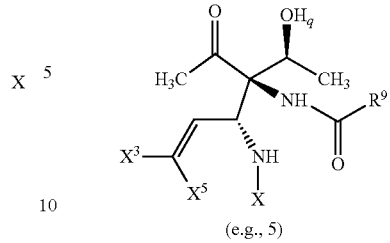

(e.g., 5)

By techniques familiar to those skilled in the art. Protection of the —OH group can be achieved with, for example, a trialkylsilyl halide or trialkylsilyl triflate. Etherification of the OH group can be achieved with, for example, an alkylating agent under basic or acidic conditions. Deoxygenation of the —OH group can be achieved by, for example, conversion to a xanthate and reduction under free radical conditions.

Compounds of Formula XII above can be made by reducing a compound of Formula XIII:

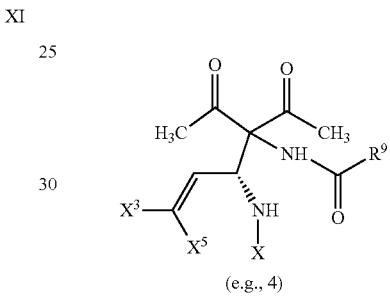

(e.g., 4)

to produce the compound of Formula XII.

Compound of Formula XIII above can be made by reacting a compound of Formula XIV:

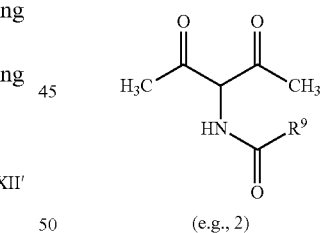

(e.g., 2)

with a compound of Formula XV:

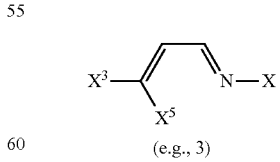

(e.g., 3)

in a Mannich reaction to produce the compound of Formula XIII. The Mannich reaction can be carried out under reaction conditions and with catalysts known to those skilled in the art. For example, suitable catalysts include, but are not limited to, the following, with selectivities as shown:

Cinchonidine 86:14
Cinchonine 25:75
Quinine 63:37
Qunidine 34:66

(DHQ)₂PHAL 40:60
(DHQD)₂PHAL racemic

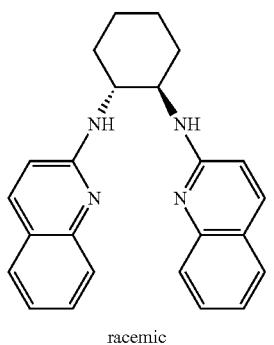
racemic

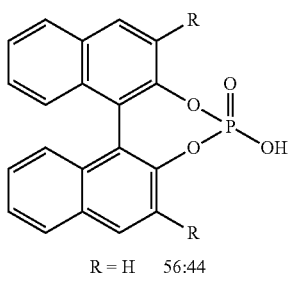
R = H 56:44
biphenyl 67:33

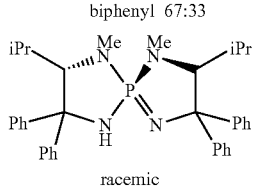
racemic

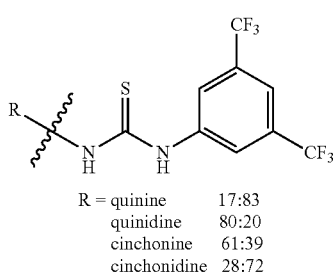
R = quinine 17:83
quinidine 80:20
cinchonine 61:39
cinchonidine 28:72

(R)-BINAP — Pd(OH)₂ — 2 TfO —
33:67

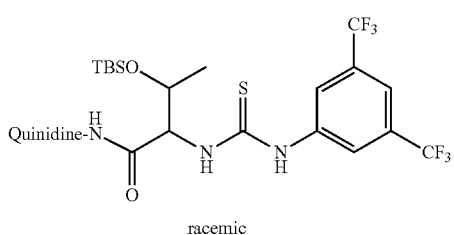
racemic

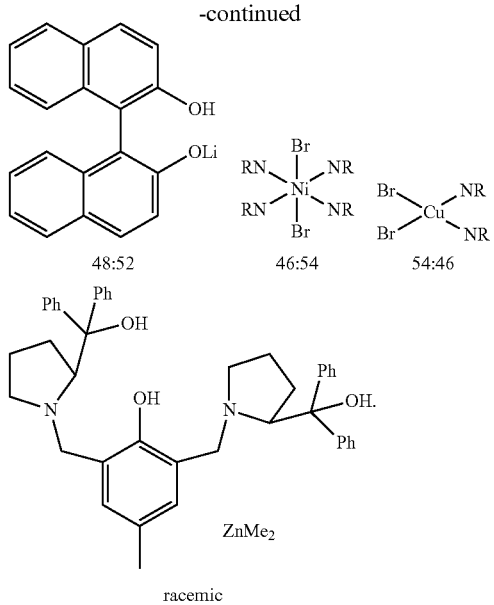
48:52    46:54    54:46 racemic

Compounds of Formula XIV and XV are known and either commercially available or can be produced in accordance with known techniques.

In additional non-limiting examples of all of the foregoing compounds and methods:

$R^5$ is meta-acetylphenyl, 3-acetyl-5-fluorophenyl, indol-3-yl, pyrazinyl, piperazinyl, 2-naphthyl, or benzimidazolyl;

$R^6$ is benzoyl, 2-hydroxy-6-methylbenzoyl, or indol-3-oyl;

$R^7$ is H, methyl, ethyl, phenyl, isobutyl, isopropyl, or n-butyl;

$R^8$ is H, OH, OSitBuMe₂, methoxy, ethoxy, or benzyloxy; and $R^9$ is dimethylamino, pyrrolidino, diethylamino, ethylmethylamino, or dibenzylamino.

Particular examples of compounds of Formula I above include, but are not limited to, the following:

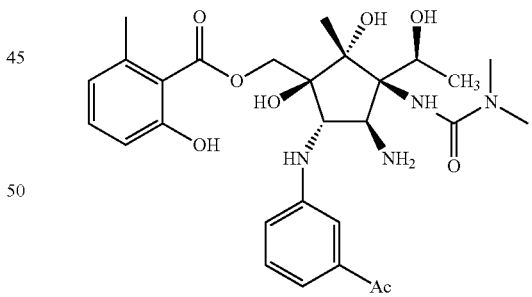
where "Ac" is acetyl

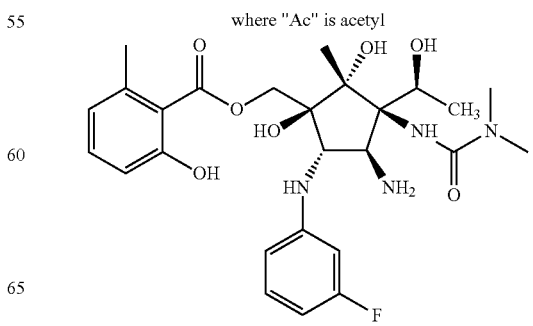

15
-continued
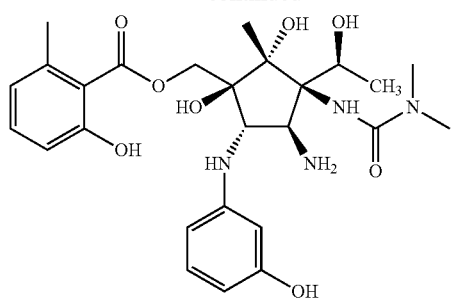
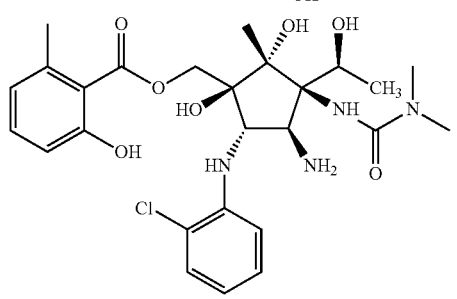
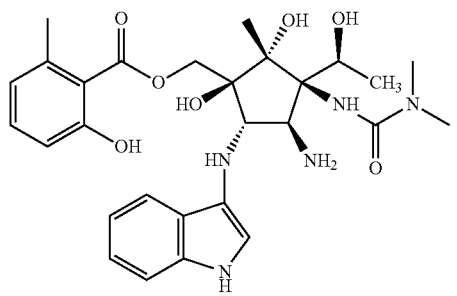
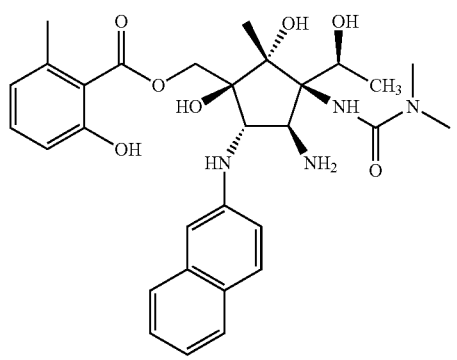
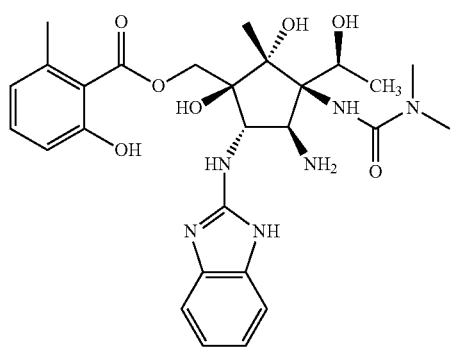
16
-continued
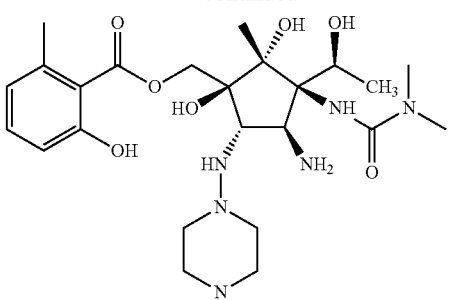
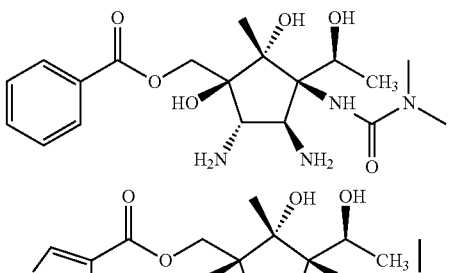
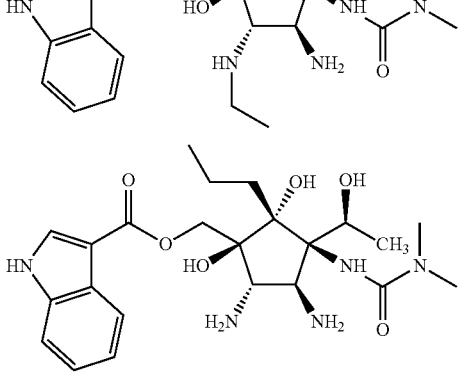
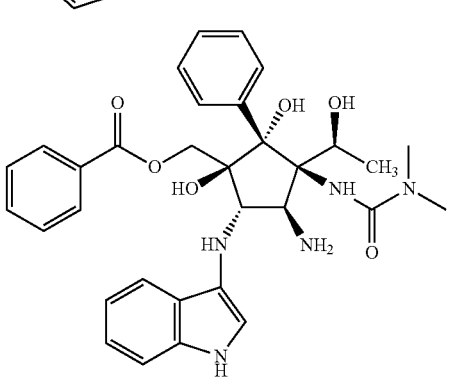
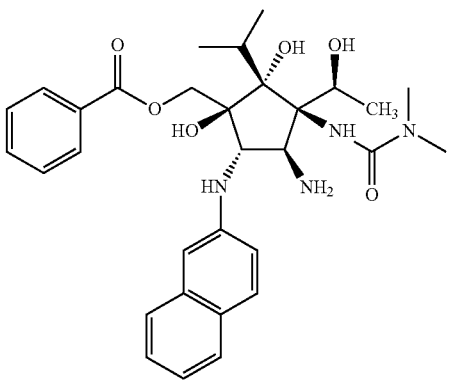

-continued

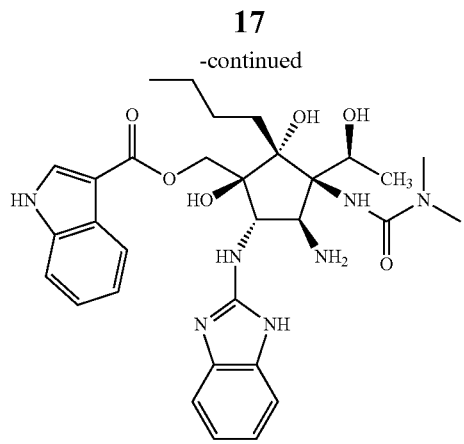

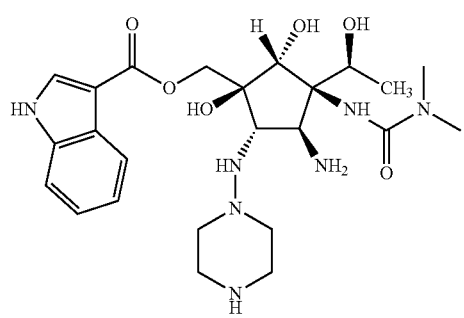

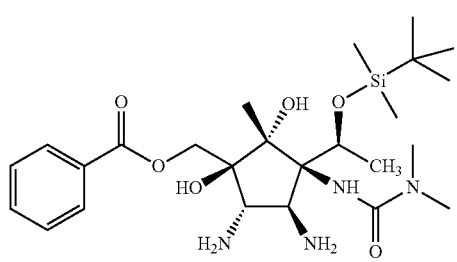

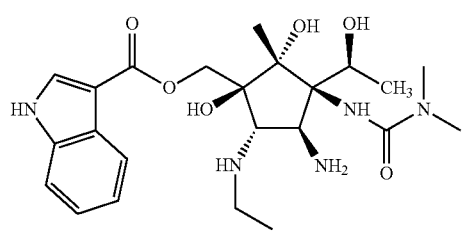

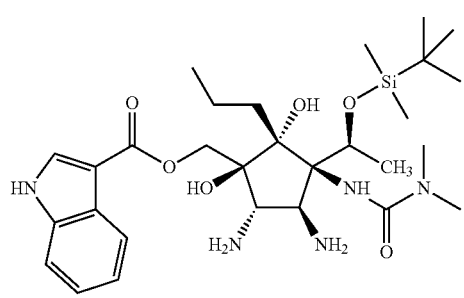

-continued

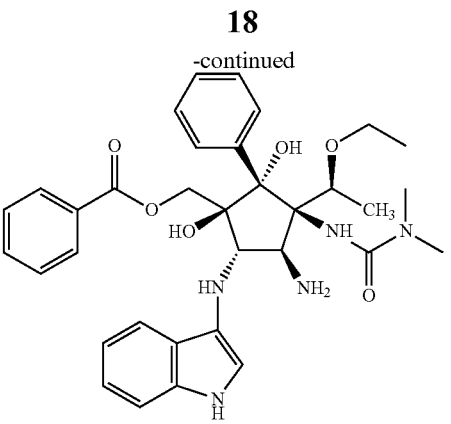

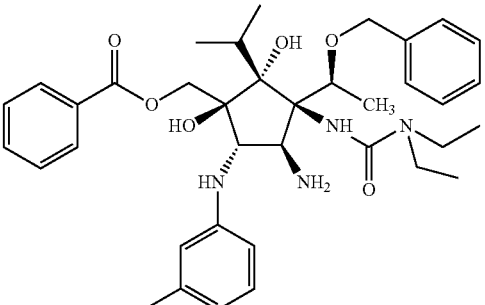

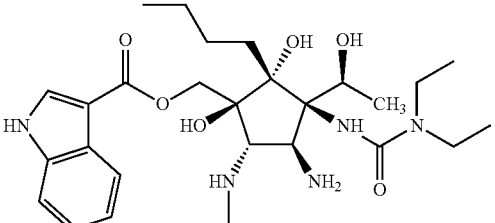

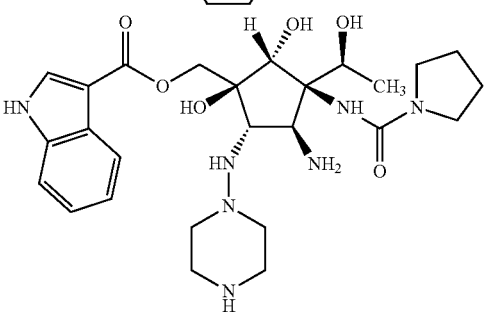

The active compounds disclosed herein can, as noted above, be provided in the form of their salts, including physiologically and pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

Active compounds as described herein can be prepared in accordance with known procedures, or variations thereof that will be apparent to those skilled in the art.

3. Pharmaceutical Formulations

The active compounds described above may be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the active compound (including the physiologically acceptable salts thereof) is typically admixed with, inter cilia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces), transdermal administration, and intraventricular injection (injection into a ventricle of the brain, e.g., by an implanted catheter or omman reservoir, such as in the case of morbid obesity) and although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis†tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

The liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to compounds of formula (I) or their salts, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

4. Methods, Dosage and Routes of Administration

The present invention is primarily concerned with the treatment of human subjects, but the invention may also be carried out on animal subjects, particularly mammalian subjects such as mice, rats, dogs, cats, livestock and horses for veterinary purposes, and for drug screening and drug development purposes. Subjects may be of any age, including infant, juvenile, adolescent, adult, and geriatric subjects.

The active compounds or compositions described above may be administered by any suitable technique, including but not limited to oral, rectal, topical, buccal, parenteral, intramuscular, intradermal, intravenous, and transdermal administration.

The active compounds may be administered to subjects in need thereof in a treatment effective amount. Such subjects include, but are not limited to, subjects afflicted with cancer (e.g., lung, breast, prostate, colorectal, pancreatic, and liver cancer, etc., and leukemia and lymphoma), protozoal or parasitic infections (e.g., *Plasmodium falciparum*, malaria, Leishmaniasis, and Chagas disease), bacterial infections (including gram negative and gram positive bacterial infections), viral infections (e.g., infections from picornaviruses or enteroviruses such as poliovirus, human rhinovirus, porcine enterovirus, and bovine enterovirus), fungal infections, etc. Compounds of the present invention can be used to treat any of the disorders or conditions described in T. Mahmud, PCT Publication No. WO2012/018854, the disclosure of which is incorporated herein by reference.

The therapeutically effective dosage or treatment effective amount of any specific compound, the use of which is in the scope of present invention, will vary somewhat from compound to compound, and patient to patient, and will depend upon the condition of the patient and the route of delivery. In general, the dosage is from about 0.1 to about 50, 100, or 200 mg/kg of subject body weight, in single or divided dosages. For oral administration, the compositions are, for example, provided in the form of a tablet containing from 0.1, 1, 5, or 10 mg of active agent, up to 400, 800, or 1000 mg of the active agent.

Active compounds may be administered as pharmaceutically acceptable prodrugs, which are those prodrugs of the active compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299 Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. No. 6,680,324 and U.S. Pat. No. 6,680,322.

The present invention is explained in greater detail in the following non-limiting Examples.

Examples

Enantioselective Synthesis of Pactamycin, a Complex Antitumor Antibiotic

Therapeutic agents produced by bacteria have been relied upon for the treatment of numerous disease types for nearly a century (1-4). Nature possesses an extraordinary capacity to provide complex organic molecules that exhibit interesting bioactivities but are practically inaccessible via synthetic organic chemistry. The gap between biosynthesis and laboratory synthesis is especially germane when a complex natural product is precluded from therapeutic application due to inherent undesired effects that might be ameliorated through chemical analog synthesis.

Scheme 1. Structure of pactamycin (1).

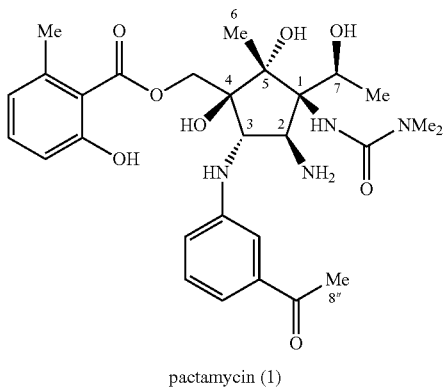

pactamycin (1)

Scheme 2.

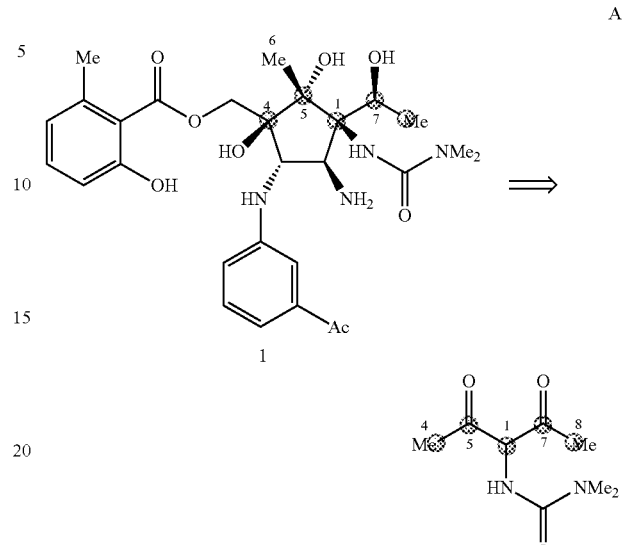

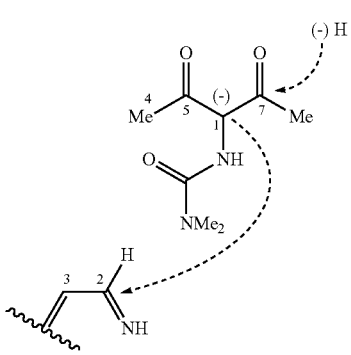

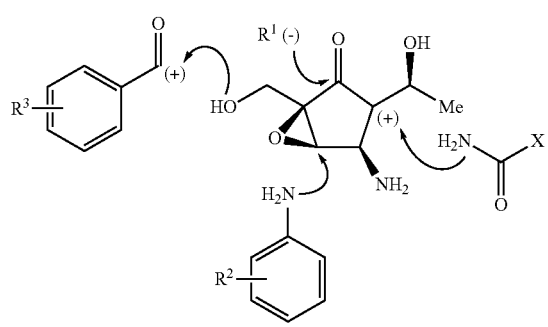

(A) Hidden symmetry recognition within pactamycin core. Semi-transparent dots highlight a 5-carbon chain from which to begin the synthesis. (B) Dashed arrows illustrate the pivotal Mannich addition and symmetry-breaking reduction steps. (C) Proposed modular construction of pactamycin. Separate components having associations indicated by arrows may be varied and introduced for analogue synthesis and SAR studies.

Pactamycin (1, Scheme 1) was isolated from *Streptomyces pactum* var *pactum* in 1961 by researchers at the Upjohn Company (5). The bioactivity profile of this natural product is remarkable as it displays antitumor, antimicrobial, antiviral, and antiprotozoal properties by acting as a universal inhibitor of translocation (6-9). Within the ribosomal subunit in which it interacts, pactamycin mimics an RNA dinucleotide through interactions of its aniline and salicylate moieties with stem loops in the 16S RNA (10), Unfortunately, therapeutic benefits have yet to be realized due to high cytotoxicity ($IC_{50}$ 95 nM) (11). Pactamycin is a prototypical example of a promising bioactive natural product whose complexity hampers investigation of structure/activity relationships (SAR) that might lead to a serviceable therapeutic and/or better understanding of intrinsic bioactivity. Biogenetic engineering studies have reignited promise for medicinal application as 7-deoxy and 8"-hydroxy derivatives were isolated and displayed diminished cytotoxicity (11-14). In the context of the work described herein, it is worth noting that Lu et al. contend that the structural complexity of 1 renders these and related structural modifications "inaccessible by synthetic organic chemistry" (12). Conversely, we have proceeded from the hypothesis that the biogenetically engineered approach to pactamycin analogs might be inherently limited by the biosynthetic machinery. A chemical approach could in principle provide far greater opportunity and flexibility for discovering and advancing useful compounds, particularly given the diverse functionality of pactamycin; however, this tactic will only be feasible in the presence of an efficient synthesis platform that rapidly develops the level of structural complexity that is present. In fact, synthetic interest in pactamycin has recently flourished, culminating in the landmark 32-step total synthesis from Hanessian and coworkers (15, 16), as well as numerous partial synthetic studies (17-21). Despite these creative, state-of-the-art approaches, a compelling case can be made that a more practical synthesis solution is needed.

We here disclose a fifteen-step total synthesis of pactamycin. Emphasis was placed on both modular construction and introduction of functionality in its final desired form, enabling an approach amenable to derivatization for analog synthesis. Late-stage introduction of the aniline and salicylate binding elements provides an opportunity for future SAR studies. These features are vital to the utilization of pactamycin and its analogs in the biomedical arena.

Critical to our synthetic plan was the recognition of a "hidden symmetry" in the northeast quadrant of pactamycin (1). Depicted in Scheme 2A, the carbon chain connecting C4 and C8 can be extracted to a symmetrical α-ureido-2,4-pentanedione 2. We envisaged simplified formation of the fully-substituted C1 center via the invention of a new Mannich reaction. Due to the symmetrical methyl ketone substituents at C1, diastereoselectivity considerations are obviated, allowing for a focus on the enantioselective C2-amino incorporation during the C1-C2 bond construction. The nascent C2 stereocenter would then need to direct a site- and diastereoselective diketone mono-reduction, setting the C2/C1/C7 stereotriad (red arrows, FIG. 2B). This sequence would provide the entire pactamycin carbon core skeleton from which modular delivery of various functionality (FIG. 2C) could provide 1 and/or its congeners in rapid fashion.

The first challenge faced was the development of a new Mannich reaction to be executed with an appropriately configured imine electrophile. While encouraged by results reported by Schaus and coworkers wherein cinchona alkaloids were effective in catalyzing the enantioselective addition of simple 1,3-dicarbonyls to acyl imines (22, 23); the required Mannich addition of α-amino-substituted dicarbonyls was heretofore unknown. Additionally, with our goal of modular construction in mind, we planned to install the unusual 1,1-dimethylurea in its native form early in our route, a tactic that was expected to obviate protection/deprotection/acylation steps that characterize all other pactamycin synthetic studies.

Pronucleophile 2 was synthesized in two steps (24) from commodity chemical acetylacetone (2.5 kg~$75) and subjected to adapted Mannich conditions with cinnamaldehyde-derived imine 3 (Scheme 3). An evaluation of Lewis bases led to selection of cinchonidine (7) as the catalyst of choice, providing Mannich product 4 in 70% isolated yield and 97:3 enantiomeric ratio (94% yield, 84:16 er before removal of the racemate by trituration). An X-ray diffraction study of a derivative (data not shown) revealed formation of the illustrated (R) configuration at C2. The reader will note that this nominally corresponds to the incorrect configuration at C2, but the advancement of this stereochemical "mistake" was in fact critical to orchestrate downstream stereochemical outcomes and efficiently complete the synthesis (vide infra). The strategic selection of cinnamyl imine 3 as the Mannich electrophile translated to the installation of all five carbons of the pactamycin core, with appropriate functional handles, in this initial C—C bond construction. While not the focus of the present investigation, it is worth noting that this reaction constitutes a useful advance in the synthesis of differentiated, highly functionalized 1,2-diamines.

Scheme 3.

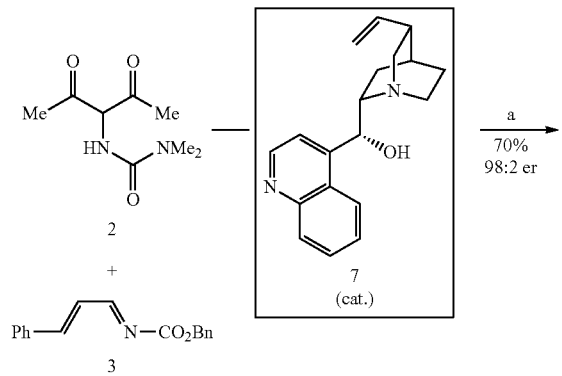

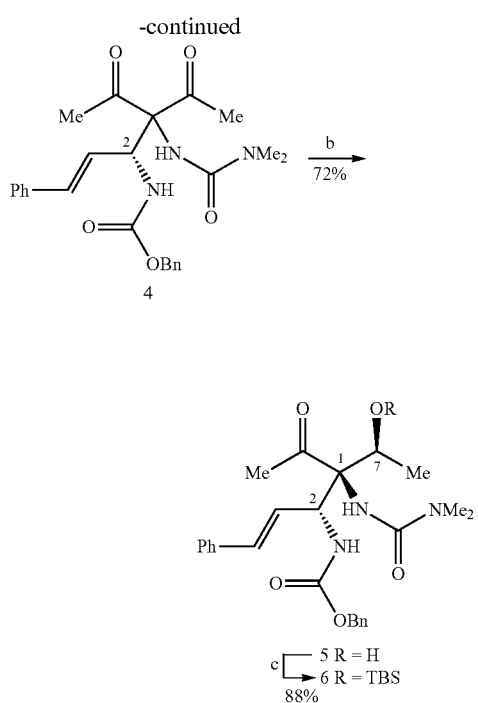

New Mannich reaction and diastereoselective diketone monoreduction. This two-step sequence installs all pactamycin core carbons as well as three contiguous stereocenters. Reagents and conditions are as follows. (a) Catalyst 7 (20 mol %), dichloromethane (CH$_2$Cl$_2$), -65° C.; (b) lithium tri(tert-butoxy)aluminum hydride (LTBA), tetrahydrofuran (THF), -40° C.; (c) tert-butyldimethylsilyl trifluoromethanesulfonate (TBSOTf), 2,6-lutidine, CH$_2$Cl$_2$, -78° C.

The proposed desymmetrization of the Mannich adduct (4→5) is complicated by the fact that four diastereomeric mono-reduction products are possible. Lithium tri(tert-butoxy)aluminum hydride (LTBA) emerged as a superior reducing agent for the desymmetrization, affording hydroxyketone 5 with high diastereoselectivity (>10:1 ratio of 5:Σ(other diastereomers)) in 72% yield. This reduction delivered the illustrated (1R,2R,7S)-product; therefore, the incorrect C2 isomer was parlayed into the correct C1/C7 configurations. Subsequent silyl protection of the C7 hydroxyl gave methyl ketone 6.

Our attention then shifted to installation of the C4 side-chain and cyclization to complete the cyclopentenone core (Scheme 4). The lithium enolate of ketone 6 was treated with formaldehyde gas resulting in the single aldol addition product 8 (24, 25). Alkene ozonolysis furnished aldehyde 9 poised for intramolecular aldol condensation. Cyclization of the β-hydroxy ketone (26) was effected upon treatment with sodium methoxide to provide the five-membered pactamycin core structure (10) in 50% yield over two steps. Under the basic reaction conditions, the configurationally labile C2 stereocenter was inverted and only the correct C2 isomer was observed in the product enone 10. This serendipitous event corrected an initial stereochemical "error," simplifying subsequent core manipulation.

Scheme 4.

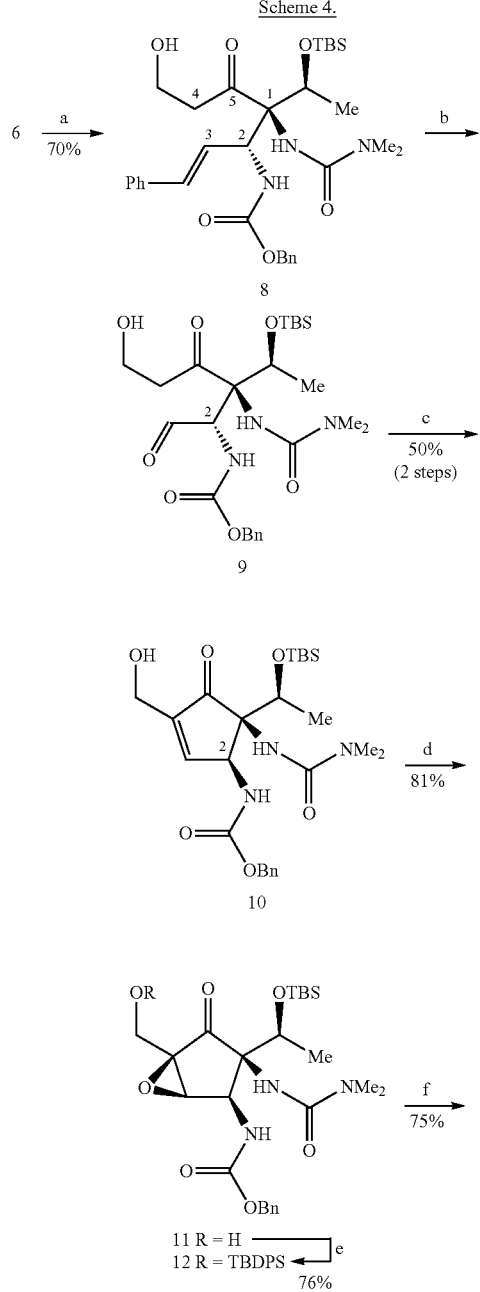

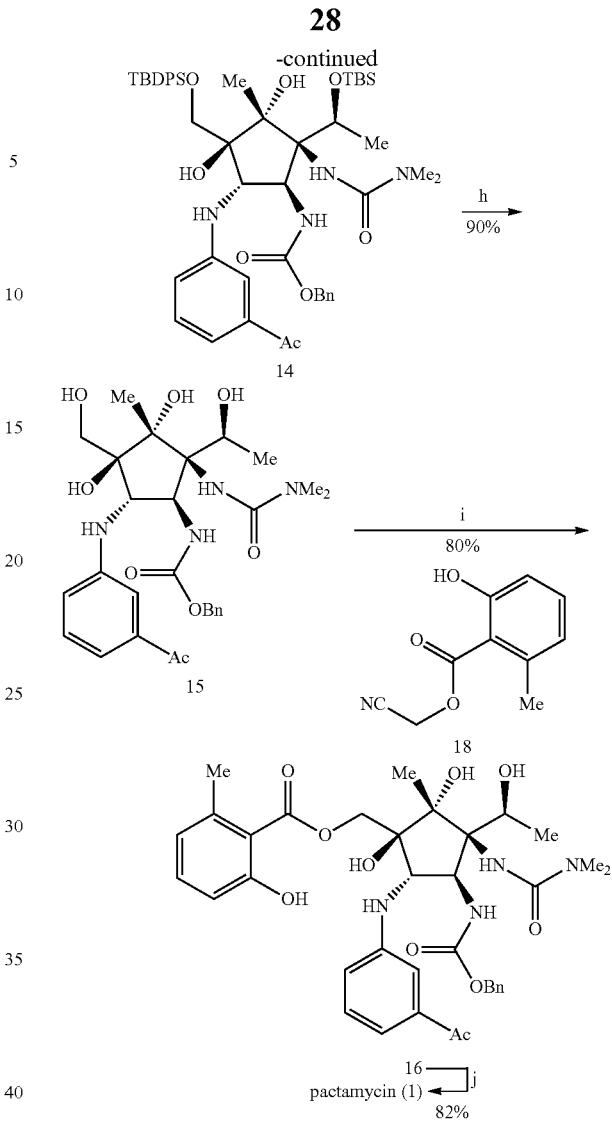

Elaboration of 6 to pactamycin (1) via modular incorporation of unprotected functionality. Reagents and conditions are as follows. (a) lithium diisopropylamide (LDA), paraformaldehyde ((CH$_2$O)$_n$), THF, -78 to -45° C.; (b) ozone (O$_3$), CH$_2$Cl$_2$, -78° C., then dimethylsulfide (Me$_2$S), -78° C. to rt; (c) sodium methoxide (NaOMe), THF, 0° C.; (d) hydrogen peroxide (H$_2$O$_2$), sodium hydroxide (NaOH), 7:1 CH$_2$Cl$_2$: methanol (MeOH), 0° C.; (e) chloro(tert-butyl)diphenylsilane (TBDPSCl), triethylamine (NEt$_3$), dimethylaminopyridine (DMAP) (10 mol %), CH$_2$Cl$_2$, 0° C. to rt; (f) methylmagnesium bromide (MeMgBr), THF, 0° C.; (g) 3-acetylaniline (17), scandium(III) trifluoromethanesulfonate (Sc(OTf)$_3$), toluene, 60° C.; (h) tetrabutylammonium fluoride (TBAF), THF, 0° C.; (i) potassium carbonate (K$_2$CO$_3$), 18, dimethylacetamide (DMA); (j) palladium hydroxide on carbon (Pd(OH)$_2$/C), hydrogen (H$_2$) (1 atm), MeOH.

With cyclopentenone 10 in hand, three challenges remained: (1) C5 methide addition, (2) C4 hydroxylation, and (3) C3 aniline installation. An epoxidation/nucleophilic aniline ring-opening sequence was pursued for access to the trans-anilinoalcohol, inspired by a related approach by Hanessian and coworkers (15, 16). Subsequent nucleophilic methylation of the C5 ketone would complete the core functionalization. As this proposed route was explored, the importance of both the order of these steps and the protecting group identity at the C4 hydroxymethylene was discovered.

Nucleophilic epoxidation of enone 10 with basic hydrogen peroxide provided epoxy alcohol 11 with high diastereoselectivity. The sterically demanding TBDPS protecting group was imperative to ensure diastereoselective addition in the subsequent C5 methylation and to withstand the aniline epoxide-opening conditions. Installation of the silyl group provided ketone 12, which was then treated with methyl Grignard to provide carbinol 13, gratifyingly from the required concave facial trajectory. Nucleophile approach from the convex surface of analogous oxobicyclo[3.1.0]hexane systems is well documented (15, 16, 27) and would have provided the wrong stereochemical outcome. In the present case, it was surmised that this innate preference is overridden via direction by the urea functionality, lending additional support to the strategic decision to incorporate this functionality in its native form from the outset. The epoxide was subjected to a Sc(OTf)$_3$-promoted nucleophilic ring-opening with 3-acetylaniline (17), proceeding in 66% yield with 18% recovery of the starting material to install the C3 aniline derivative. The addition of this anilino functionality in its desired, unprotected form completed functionalization of the pactamycin core (14).

Deprotection of both silyl ethers was accomplished upon treatment with TBAF to provide tractable tetraol 15 in 90% yield, leaving a highly reactive primary alcohol for selective acylation. A ketene-mediated acylation protocol developed by Delgado (28) and exploited by Hanessian (15, 16) proved effective in completing the sterically encumbered acylation and providing penultimate intermediate 16. Carboxybenzyl deprotection occurred rapidly under hydrogenolysis conditions using Pearlman's catalyst (29) to give pactamycin in 82% yield.

Methods: General.

Infrared (IR) spectra were obtained using a Jasco 460 Plus Fourier transform infrared spectrometer. Proton and carbon magnetic resonance spectra ($^1$H NMR and $^{13}$C NMR) were recorded on a Bruker model Avance 500 ($^1$H NMR at 500 MHz and $^{13}$C NMR at 125 MHz) or a Bruker Avance III 600 ($^1$H NMR at 600 MHz and $^{13}$C NMR at 150 MHz) spectrometer with solvent resonance as the internal standard ($^1$H NMR: CDCl$_3$ at 7.26 ppm; $^{13}$C NMR: CDCl$_3$ at 77.0 ppm). $^1$H NMR data are reported as follows: chemical shift, multiplicity (s=singlet, br s=broad singlet, d=doublet, br d=broad doublet, t=triplet, q=quartet, m=multiplet), coupling constants (Hz), and integration. Mass spectra were obtained using a Micromass Quattro-II triple quadrupole mass spectrometer in combination with an Advion NanoMate chip-based electrospray sample introduction system and nozzle or a Thermo LTqFT mass spectrometer with electrospray introduction and external calibration. All samples were prepared in methanol. Analytical thin layer chromatography (TLC) was performed on Sorbent Technologies 0.20 mm Silica Gel TLC plates. Visualization was accomplished with UV light, KMnO$_4$, and/or aqueous eerie ammonium nitrate solution followed by heating. Purification of the reaction products was carried out by flash chromatography using Siliaflash-P60 silica gel (40-63 µm) purchased from Silicycle. Supercritical fluid chromatography was performed on a Berger SFC system equipped with a Chiralcel OD column. Samples were eluted with SFC grade CO$_2$ at the indicated percentage of MeOH. Unless otherwise noted, all reactions were carried out under an atmosphere of dry nitrogen in oven-dried glassware with magnetic stirring. Yield refers to isolated yield of analytically pure material unless otherwise noted. Yields are reported for a specific experiment and as a result may differ slightly from those found in Figures, which are averages of at least two experiments.

Materials: General.

Tetrahydrofuran (THF), diethyl ether (Et$_2$O), dichloromethane (CH$_2$Cl$_2$), and toluene were dried by passage through a column of neutral alumina under nitrogen prior to use. Triethylamine (NEt$_3$) and diisopropylamine were freshly distilled from calcium hydride prior to use. Cinnamaldehyde was distilled under reduced pressure and elevated temperature immediately prior to use. Imine 3 and cyanomethyl ester 18 were prepared by known procedures (B. M. Trost, D. W. Lupton, Org. Lett. 9, 2023 (2007); S. Hanessian et al., Angew. Chem., Int. Ed, 50, 3497 (2011).). All other reagents were purchased from commercial sources and were used as received unless otherwise noted.

Experimental Procedures

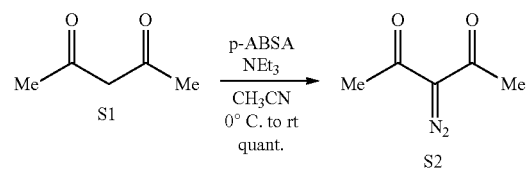

3-diazopentane-2,4-dione (S2)

A 1-L round-bottomed flask was charged with acetylacetone (S1) (10.25 mL, 100 mmol, 1.0 equiv) and acetonitrile (600 mL). p-Acetamidobenzene sulfonyl azide (p-ABSA)(J. S. Baum et al., Synth. Commun. 17, 1709 (1987) (24.0 g, 100 mmol, 1.0 equiv) was added and the reaction was cooled to 0° C. Triethylamine (NEt$_3$) (41.8 mL, 300 mmol, 3 equiv) was added dropwise and the reaction was warmed to rt for 1 hour. The resulting suspension was filtered through a fitted funnel and concentrated. The obtained residue was triturated with 1:1 ether:petroleum ether and the precipitated white solids were removed via filtration. Solvents were removed in vacuo providing analytically pure S2 as a yellow oil in quantitative yield. Spectral data matched those reported in the literature (Z.-B. Chem et al., J. Org. Chem. 74, 903 (2009)).

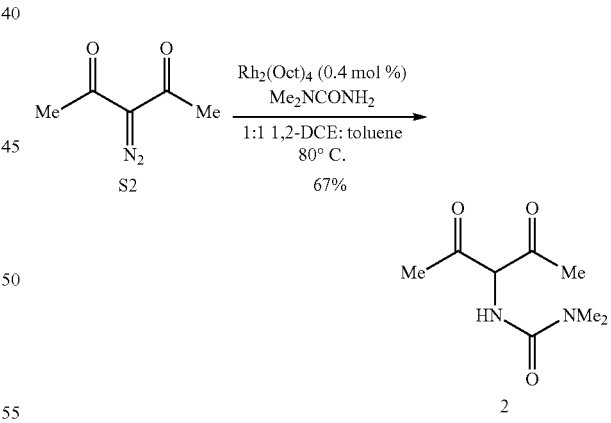

3-(2,4-dioxopentan-3-yl)-1,1-dimethylurea (2)

A 1-L round-bottomed flask was charged with finely ground 1,1-dimethylurea (21.0 g, 237.0 mmol, 1.5 equiv). Toluene (400 mL) and 1,2-dichlorethane (400 mL) were added followed by diazodiketone S2 (20 g, 158.0 mmol, 1.0 equiv). The suspension was heated to 80° C. in a sand bath with magnetic stirring and gradually became homogeneous. Rh$_2$(Oct)$_4$ (0.492 g, 0.632 mmol, 0.004 equiv) suspended in toluene (10 mL) was added in four portions over 30 min. The reaction temperature was maintained at 80° C. and stirred until complete consumption of S2 was indicated by TLC analysis, typically 1 h. The reaction was allowed to cool to rt, precipitating the excess 1,1-dimethylurea. Solids were removed by vacuum filtration and the filtrate was concentrated in vacuo. The crude product was purified via flash chromatography (70:30 to 60:40 petroleum ether/acetone) to provide the title compound as a yellow solid (19.8 g, 67%). Note: NMR analyses typically showed a ~2:1 mixture of enol:keto tautomers. Analytical data: trip 105-109° C.; $^1$H NMR (600 MHz, CDCl$_3$): keto-tautomer: δ 5.92 (br s, 1H), 5.03 (d, J=4.8 Hz, 1H), 2.92 (s, 6H), 2.20 (s, 6H); enol-tautomer: δ 15.77 (s, 1H), 5.99 (s, 1H), 2.94 (s, 6H), 2.03 (s, 6H); $^{13}$C NMR (150 MHz, CDCl$_3$): δ 201.7, 191.8, 157.5, 157.2, 112.3, 72.8, 36.5, 36.3, 36.2, 27.2, 23.9, 21.9; LRMS (ESI$^+$) Calcd. for C$_8$H$_{14}$N$_2$O$_3$+Na, 209.09. Found, 209.04. IR (thin film, cm$^{-1}$) 3419, 2360, 2126, 1636, 1317, 1315, 1022, 914, 889; TLC (60:40 petroleum ether/acetone): R$_f$=0.30.

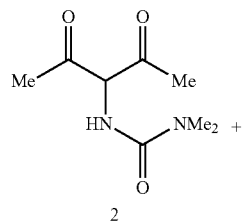

urea 2 was indicated by TLC analysis, typically 14-36 h (scale-dependent). The crude reaction was filtered through a short silica plug and rinsed with EtOAc (300 mL). The filtrate was concentrated in vacuo to give a pale yellow foam with a 84:16 enantiomeric ratio. Crystalline racemic product was isolated via trituration with 60:40 (v/v) hexanes:EtOAc (300 mL). The analytically-pure white solid was removed by filtration (1.33 g, 24%) and the filtrate was concentrated in vacuo to give a yellow oil. The crude oil was purified by flash chromatography (60:40 to 50:50 hexanes:EtOAc) affording diketone 4 as a pale yellow foam (3.87 g, 70%, 97:3 er). The enantiomeric ratio (er) was determined by SFC analysis (Chiralcel, OD, 9.0% MeOH, 1.5 mL/min, 150 bar, 210 nm; t$_R$-minor 12.8 min, t$_R$-major 14.7 min). Analytical data: [α]$_D^{19}$ +16.5 (c=1.00, CHCl$_3$); mp (racemate) 130-134° C.; $^1$H NMR (600 MHz, CDCl$_3$): δ 7.37-7.21 (m, 10H), 7.07 (br d, J=6.0 Hz, 1H), 6.59 (d, J=16.2 Hz, 1H), 6.50 (s, 1H), 5.96 (dd, J=16.2 Hz, 7.2, 1H), 5.40 (t, J=7.2 Hz, 1H), 5.14 (d, J=12.0 Hz, 1H), 5.11 (d, J=12.0 Hz, 1H), 2.97 (s, 6H), 2.28 (s, 3H), 2.14 (s, 3H); $^{13}$C NMR (150 MHz, CDCl$_3$): δ 200.9, 200.4, 157.6, 156.7, 136.9, 136.5, 133.2, 128.7, 128.6, 128.2, 128.2, 128.1, 126.9, 124.6, 81.7, 67.0, 57.2, 36.8, 26.2, 25.4; LRMS (ESI$^+$) Calcd. For C$_{25}$H$_{29}$N$_3$O$_5$+Na, 474.20. Found, 474.22. IR (thin film, cm$^{-1}$) 3418, 2243, 1702, 1635, 1507, 1371, 1249, 1066, 912, 693; TLC (60:40 Hexanes:EtOAc): R$_f$=0.20.

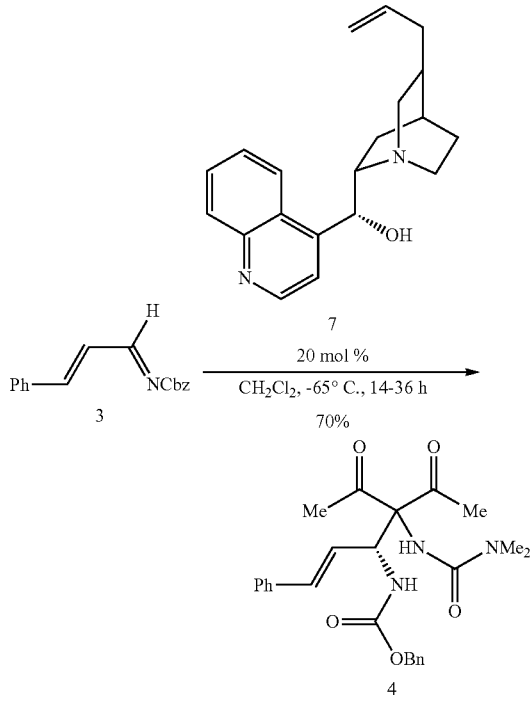

(R,E)-benzyl (4-acetyl-4-(3,3-dimethylureido)-5-oxo-1-phenylhex-1-en-3-yl)carbamate (4)

A flame-dried 250-mL round-bottomed flask was charged with urea 2 (2.38 g, 12.28 mmol, 1.0 equiv), cinchonidine (7) (0.72 g, 2.46 mmol, 0.2 equiv), and CH$_2$Cl$_2$ (65 mL). The resulting suspension was cooled to −78° C. and a cold solution of imine 3 (5.1 g, 19.24 mmol, 1.5 equiv) in CH$_2$Cl$_2$ (35 mL) was added via cannula transfer. The reaction was warmed to −65° C. and stirred until complete consumption of

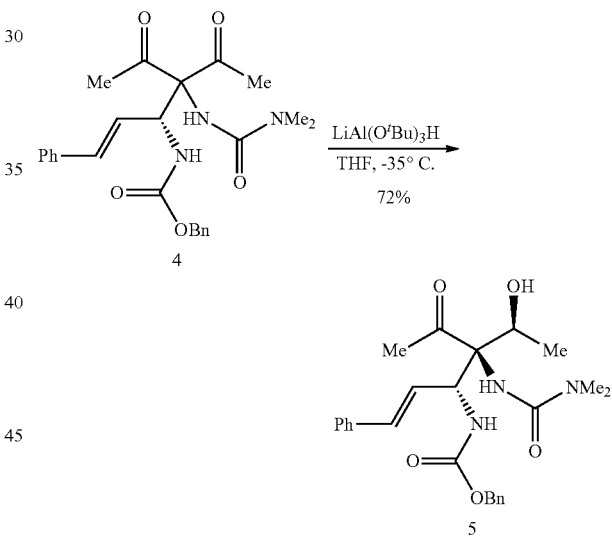

Benzyl ((3R,4R,5S,E)-4-acetyl-4-(3,3-d ethylureido)-5-hydroxy-1-phenylhex-1-en-3-yl) carbamate (5)

A flame-dried 250-mL round-bottomed flask was charged with diketone 4 (8.5 g, 18.8 mmol, 1.0 equiv) and THF (188 mL). The solution was cooled to −78° C., and lithium tri-tert-butoxyaluminum hydride (1.1 M in THF, 25.7 mL, 28.2 mmol, 1.5 equiv) was added dropwise. The resulting mixture was warmed to −35° C. and stirred until complete consumption of diketone 4 was indicated by TLC analysis, typically 12 h. The reaction was quenched by the addition of a saturated NH$_4$Cl$_{(aq.)}$ (50 mL) and the biphasic mixture was extracted with EtOAc (3×50 mL). The combined organic extracts were washed with brine (50 mL), dried with magnesium sulfate, and concentrated in vacuo. The crude product was purified via flash chromatography (50:50 to 60:40 EtOAc/hexanes) to afford alcohol 5 as a yellow viscous oil with >10:1 ratio of 5:Σ(other diastereomers) (6.2 g, 72%). Analytical data: $[\alpha]_D^{19}$ +19.5 (c=1.00, CHCl$_3$); $^1$H NMR (600 MHz, CDCl$_3$): δ 7.36-7.25 (m, 10H), 6.67 (d, J=16.2 Hz, 1H), 6.59 (br s, 1H), 6.17 (dd, J=15.6, 9.0 Hz, 1H), 5.47 (s, 1H), 5.11 (d, J=12.0 Hz, 1H), 5.07 (d, J=12.0 Hz, 1H), 4.70 (t, J=9.0 Hz, 1H), 4.60 (br s, 1H), 4.30 (br s, 1H), 2.90 (s, 6H), 2.28 (s, 3H), 1.23 (d, J=6.6 Hz, 3H); $^{13}$C NMR (150 MHz, CDCl$_3$): δ 207.9, 158.4, 156.1, 136.2, 135.9, 133.8, 128.5, 128.3, 128.0, 127.9, 127.8, 126.5, 125.5, 73.7, 69.8, 66.8, 57.2, 36.5, 27.6, 18.6; LRMS (ESI$^+$) Calcd. for C$_{25}$H$_{31}$N$_3$O$_5$+Na, 476.22. Found, 476.25. IR (thin film, cm$^{-1}$) 3410, 2938, 2359, 2248, 1700, 1637, 1520, 1235, 909, 731; TLC (50:50 hexanes:EtOAc): R$_f$=0.20.

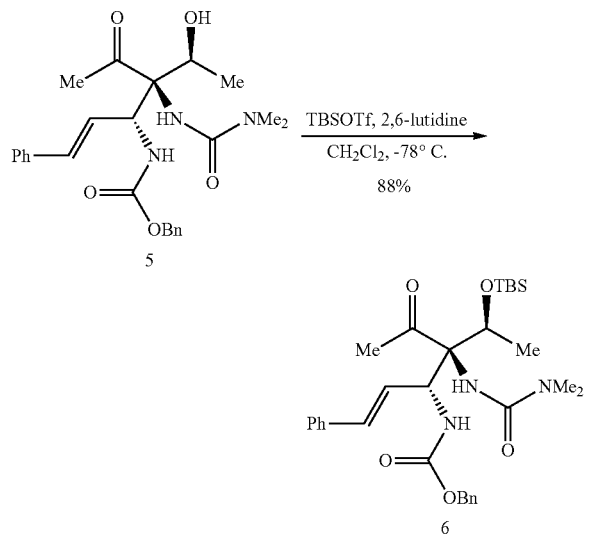

Benzyl ((3R,4R,5S,E)-4-acetyl-5-((tert-butyldimethylsilyl)oxy)-4-(3,3-dimethylureido)-1-phenylhex-1-en-3-yl)carbamate (6)

A flame-dried 100-mL round-bottomed flask was charged with alcohol 5 (6.2 g, 13.6 mmol, 1.0 equiv) and CH$_2$Cl$_2$ (68 mL). 2,6-Lutidine (4.7 mL, 40.7 mmol, 3.0 equiv) was added and the solution was cooled −78° C. TBSOTf (3.7 mL, 16.3 mmol, 1.2 equiv) was added dropwise and the reaction was stirred for 30 min at −78° C., Saturated NaHCO$_3$$_{(aq.)}$ (30 mL) and EtOAc (30 mL) were added and the reaction was allowed to warm to rt. The layers were separated and the aqueous portion was extracted with EtOAc (3×50 mL). The combined organic extracts were washed with 1M HCl (30 mL) and brine (30 mL), and dried with magnesium sulfate. The crude product was concentrated in vacuo and purified via flash chromatography (20:80 to 30:70 EtOAc:hexanes) to give the title compound as a pale yellow oil (6.8 g, 88%). Analytical data: $[\alpha]_d^{19}$ −1.5 (c=1.00, CHCl$_3$); $^1$H NMR (600 MHz, CDCl$_3$): δ 7.37-7.27 (m, 10H), 7.22 (t, J=7.2 Hz, 1H), 6.63 (d, J=16.2 Hz, 1H), 6.32 (dd, J=16.2, 7.8 Hz, 1H), 5.31 (s, 1H), 5.11 (d, J=12.6 Hz, 1H), 5.06 (d, J=12.6 Hz, 1H), 5.03 (t, J=8.4 Hz, 1H), 4.48 (q, J=6.0 Hz, 1H), 2.96 (s, 6H), 2.22 (s, 3H), 1.22 (d, J=6.0 Hz, 3H), 0.88 (s, 9H), 0.10 (s, 3H), 0.09 (s, 3H); $^{13}$C NMR (150 MHz, CDCl$_3$): δ 205.2, 158.8, 155.7, 136.8, 136.6, 132.2, 128.2, 128.1, 127.7, 127.6, 127.3, 127.1, 126.4, 71.2, 66.3, 54.8, 36.5, 26.5, 25.5, 19.1, 17.7, −3.9, −5.2; LRMS (ESI$^+$) Calcd. for C$_{31}$H$_{45}$N$_3$O$_5$Si+H, 568.32. Found, 568.33. IR (thin film, cm$^{-1}$) 3417, 2954, 1857, 1714, 1651, 1517, 1253, 1128, 1063, 837, 737; TLC (75:25 hexanes/EtOAc): R$_f$=0.30.

Benzyl ((3R,4R,E)-4-((S)-1-((tert-butyldimethylsilyl)oxy)ethyl)-4-(3,3-dimethylureido)-7-hydroxy-5-oxo-1-phenylhept-1-en-3-yl)carbamate (8)

A flame-dried 250-mL round-bottomed flask was charged with diisopropylamine (5.8 mL, 41.3 mmol, 3.5 equiv) and THF (100 mL). The resulting solution was cooled to 0° C. and n-butyllithium (1.65 M in hexanes, 25.0 mL, 41.3 mmol, 3.5 equiv) was added dropwise. The reaction was stirred at 0° C. for 30 min and then cooled to −78° C. A solution of ketone 6 (6.8 g, 11.8 mmol, 1.0 equiv) in THF (25 mL) was added dropwise, and the resulting mixture was stirred for 45 min and warmed to −45° C. Formaldehyde gas (CH$_2$O$_{(g)}$, prepared by heating paraformaldehyde ((CH$_2$O)$_n$, 5.0 g, 166.7 mmol, 14.1 equiv) to 145° C. under a positive pressure of nitrogen) was bubbled through the reaction. The reaction was stirred at −45° C. until full conversion to product was indicated by TLC analysis, typically 1 h. The reaction was quenched by the addition of a saturated NH$_4$Cl$_{(aq.)}$ (30 mL), and the resulting mixture was extracted with Et$_2$O (3×30 mL). The combined organic extracts were dried with magnesium sulfate and concentrated in vacuo. The crude product was purified via flash chromatography (50:50 to 60:40 EtOAc:hexanes) to give alcohol 8 as a clear, viscous oil (4.9 g, 70%). Analytical data: $[\alpha]_D^{19}$ +11.2 (c=1.00, CHCl$_3$); $^1$H NMR (500 MHz, CDCl$_3$): δ 7.35-7.26 (m, 10H), 7.21 (t, J=7.0 Hz, 1H), 6.59 (d, J=16.0 Hz, 1H), 6.28 (dd, J=16.0, 9.0, 1H), 5.32 (s, 1H), 5.11 (d, J=12.0 Hz, 1H), 5.02 (d, J=12.0 Hz, 1H), 4.98 (t, J=8.5 Hz, 1H), 4.40 (q, J=6.5 Hz, 1H), 3.85-3.82 (m, 1H), 3.73-3.71 (m, 1H), 2.93 (s, 6H), 2.82-2.70 (m, 2H), 1.23 (d, J=6.5 Hz, 3H), 0.87 (s, 9H), 0.10 (s, 3H), 0.09 (s, 3H); $^{13}$C NMR (150 MHz, CDCl$_3$): δ 208.5, 158.7, 155.9, 136.8, 136.6, 132.3, 128.4, 128.3, 128.1, 127.9, 127.5, 127.1, 126.6, 74.2, 71.7, 66.6, 58.1, 55.2, 40.7, 36.6, 25.7, 19.2, 17.8, −3.7, −5.0; LRMS (ESI$^+$) Calcd. for C$_{32}$H$_{47}$N$_3$O$_6$Si+H, 598.33. Found, 598.32. IR (thin film, cm$^{-1}$) 3429, 2954, 1716, 1646, 1507, 1252, 966, 695, 530; TLC (50:50 hexanes:EtOAc): R$_f$=0.20.

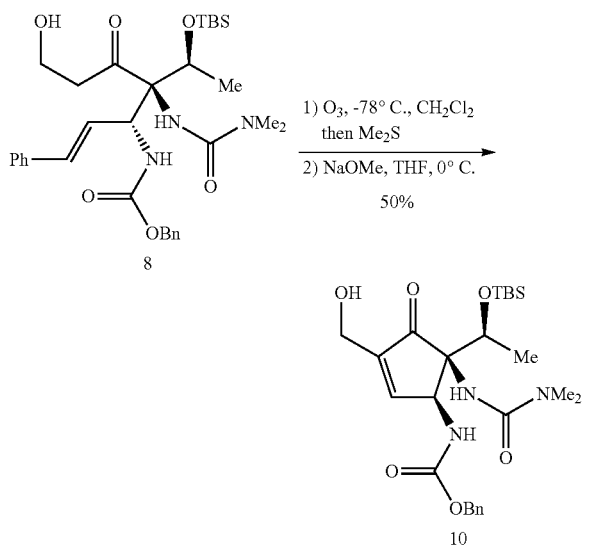

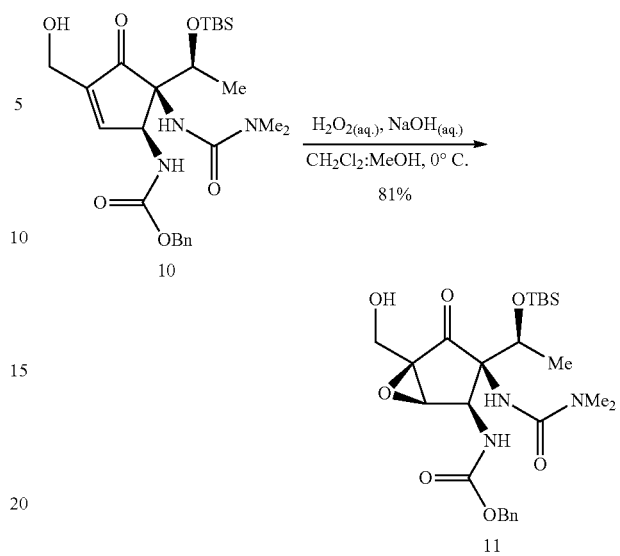

Benzyl ((1S,5R)-5-((S)-1-((tert-butyldimethylsilyl)oxy)ethyl)-5-(3,3-dimethylureido)-3-(hydroxymethyl)-4-oxocyclopent-2-en-1-yl)carbamate (10)

A 250-mL round-bottomed flask was charged with alcohol 8 (2.5 g, 4.1 mmol, 1.0 equiv) and $CH_2Cl_2$ (82 mL). The resulting solution was cooled to −78° C., and a stream of ozone ($O_3$) was bubbled through the solution until a blue color was observed, typically 5-15 min (scale dependent). The mixture was sparged with $O_2$ for 5 min, and $Me_2S$ (1.2 mL, 16.4 mmol, 4.0 equiv) was added. The reaction was warmed to rt, stirred for 12 h, and concentrated in vacuo affording the crude aldehyde (9) as a yellow oil. The unpurified product was taken on directly to the next step.

Aldehyde 9 was dissolved in THF (103 mL) and cooled to 0° C. Sodium methoxide (NaOMe) (0.5 M in MeOH, 24.6 mL, 12.3 mmol, 3.0 equiv) was added dropwise. The reaction was stirred at 0° C. until TLC analysis indicated complete consumption of the aldehyde, typically 30 min. The reaction was quenched by the addition of saturated $NaHCO_{3(aq.)}$ (30 mL), and the mixture was extracted with EtOAc (3×20 mL). The combined organic extracts were washed with brine (20 mL), dried with magnesium sulfate, and concentrated in vacuo. The product was purified by flash chromatography (70:30 to 50:50 petroleum ether:acetone) to afford enone 10 as a pale yellow, viscous oil with >20:1 diastereoselection (1.02 g, 50%). Evidence for inversion of the carbamate methine (C2 in pactamycin numbering; C1 in the IUPAC name given as the title for this experimental) during this condensation was found in a NOESY analysis of epoxide 11 and by ultimate conversion to pactamycin. Analytical data: $[\alpha]_D^{19}$ −25.9 (c=1.00, $CHCl_3$); $^1$H NMR (600 MHz, $CDCl_3$): δ 7.35-7.29 (m, 5H), 7.22 (d, J=1.2, 1H), 5.47 (d, J=10.2 Hz, 1H), 5.21 (d, J=12.0 Hz, 1H), 5.08 (s, 1H), 5.06 (d, J=10.2 Hz, 1H), 4.97 (d, J=12.0 Hz, 1H), 4.41 (s, 2H), 4.03 (q, J=6.6 Hz, 1H), 2.75 (s, 6H), 1.04 (d, J=6.6 Hz, 3H), 0.89 (s, 9H), 0.12 (s, 3H), 0.10 (s, 3H); $^{13}$C NMR (150 MHz, $CDCl_3$): δ 203.3, 158.3, 155.9, 151.8, 146.5, 136.8, 128.4, 128.0, 128.0, 71.9, 68.5, 66.3, 57.3, 54.1, 36.3, 25.5, 18.1, 17.8, −3.7, −4.9; LRMS (ESI$^+$) Calcd. for $C_{25}H_{39}N_3O_6Si+Na$, 528.25. Found, 528.28. IR (thin film, cm$^{-1}$) 3431, 2953, 2857, 2125, 1715, 1634, 1514, 1220, 928, 830; TLC (35:65 Hexanes:EtOAc): $R_f$=0.20.

Benzyl ((1R,2R,3R,5R)-3-((S)-1-((tert-butyldimethylsilyl)oxy)ethyl)-3-(3,3-dimethylureido)-5-(hydroxymethyl)-4-oxo-6-oxabicyclo[3.1.0]hexan-2-yl)carbamate (11)

A 200-mL round-bottomed flask was charged with enone 10 (1.1 g, 2.2 mmol, 1.0 equiv) and MeOH:$CH_2Cl_2$ (7:1, 32 mL). The resulting solution was cooled to 0° C., and a cooled solution of $H_2O_2$ (30% aq., 20 mL) and NaOH (20% aq., 5 mL) was added dropwise. The reaction was stirred at 0° C. for 2 h, and diluted with $Et_2O$ (30 mL). The layers were separated and the aqueous layer was extracted with $Et_2O$ (3×15 mL). The combined organics were washed with $H_2O$ (3×30 mL), brine (20 mL), dried with magnesium sulfate, and concentrated in vacuo. The crude product was purified via flash chromatography (70:30 petroleum ether:acetone) affording the title compound as a clear, viscous oil with >20:1 diastereoselection (0.91 g, 81%). Analytical data: $[\alpha]_D^{19}$ −22.4 (c=1.00, $CHCl_3$); $^1$H NMR (600 MHz, $CDCl_3$): δ 7.32-7.26 (m, 5H), 5.66 (d, J=9.6 Hz, 1H), 5.20 (d, J=12.0 Hz, 1H), 4.93 (d, J=12.6 Hz, 1H), 4.68 (s, 1H), 4.68-4.66 (m, 1H), 4.07-4.04 (m, 2H), 4.02-3.98 (m, 2H), 2.64 (s, 6H), 1.15 (d, J=6.6 Hz, 3H), 0.89 (s, 9H), 0.11 (s, 3H), 0.10 (s, 3H); $^{13}$C NMR (150 MHz, $CDCl_3$): δ 204.4, 156.9, 156.0, 136.6, 128.3, 128.1, 128.0, 74.0, 69.3, 66.4, 65.9, 60.7, 56.0, 52.3, 36.1, 25.5, 18.2, 17.7, −3.9, −4.8; LRMS (ESI$^+$) Calcd. for $C_{25}H_{39}N_3O_7Si+$, 522.26. Found, 522.23. IR (thin film, cm$^{-1}$) 3402, 2954, 2857, 2359, 2249, 2125, 1650, 1519, 1227, 830, 732; TLC (70:30 petroleum ether/acetone): $R_f$=0.30.

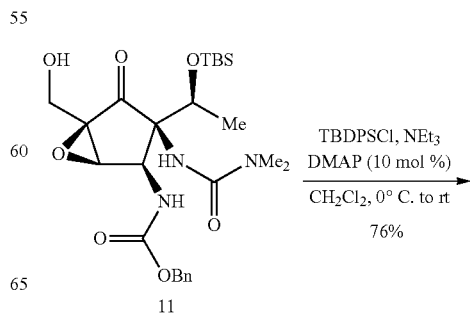

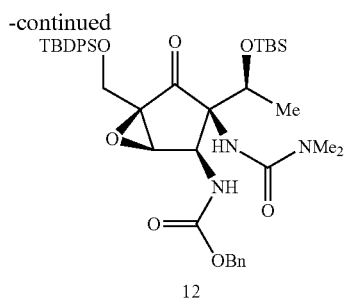
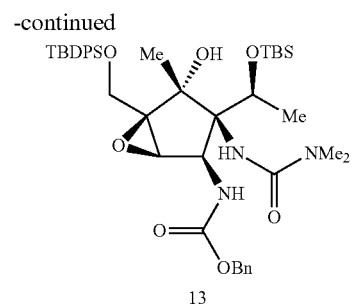

Benzyl ((1R,2R,3R,5R)-3-((S)-1-((tert-butyldimethylsilyl)oxy)ethyl)-5-(((tert-butyldiphenylsilyl)oxy)methyl)-3-(3,3-dimethylureido)-4-oxo-6-oxabicyclo[3.1.0]hexan-2-yl)carbamate (12)

A flame-dried 25-mL round-bottomed flask was charged with alcohol 11 (1.0 g, 1.9 mmol, 1.0 equiv) and CH$_2$Cl$_2$ (9.5 mL). NEt$_3$ (0.8 mL, 5.7 mmol, 3.0 equiv) and DMAP (0.023 g, 0.19 mmol, 0.1 equiv) were added and the solution was cooled 0° C. TBDPSCl (1.47 mL, 5.7 mmol, 3.0 equiv) was added dropwise and the reaction was warmed to rt and stirred for 8 h. Saturated NH$_4$Cl$_{(aq.)}$ (10 mL) was added and the mixture was extracted with Et$_2$O (3×15 mL). The combined organic extracts were washed with brine (10 mL), dried with magnesium sulfate, and concentrated in vacuo. The crude product was purified via flash chromatography (70:30 hexanes:EtOAc) to give the title compound as a pale yellow oil (1.1 g, 76%). Analytical data: $[\alpha]_D^{19}$ −4.4 (c=0.70, CHCl$_3$); $^1$H NMR (600 MHz, CDCl$_3$): δ 7.67 (d, J=7.2 Hz, 2H), 7.62 (d, J=7.2 Hz, 2H), 7.44-7.30 (m, 11H), 5.68 (d, J=10.2 Hz, 1H), 5.23 (d, J=12.0 Hz, 1H), 4.97 (d, J=12.6 Hz, 1H), 4.74 (dd, J=3.0, 7.2 Hz, 1H), 4.70 (br s, 1H), 4.26 (d, J=12, 6 Hz, 1H), 4.11 (d, J=3.0 Hz, 1H), 4.03 (q, J=6.0 Hz, 1H), 3.92 (d, J=12.0 Hz, 1H), 2.68 (s, 6H), 1.19 (d, J=6.0 Hz, 3H), 1.01 (s, 9H), 0.92 (s, 9H), 0.13 (s, 6H); $^{13}$C NMR (150 MHz, CDCl$_3$): δ 203.9, 156.8, 156.0, 136.7, 135.5, 135.4, 132.6, 132.3, 129.8, 129.7, 128.3, 128.1, 127.9, 127.8, 127.7, 74.1, 69.4, 66.4, 66.2, 60.8, 57.5, 52.2, 36.1, 26.6, 25.6, 19.1, 18.3, 17.8, −3.8, −4.8; LRMS (ESI$^+$) Calcd. for C$_{41}$H$_{57}$N$_3$O$_7$Si$_2$+H, 760.38. Found, 760.31. IR (thin film, cm$^{-1}$) 3419, 2931, 2857, 2359, 1716, 1651, 1507, 1226, 1113, 828, 733; TLC (70:30 hexanes/EtOAc): R$_f$=0.30.

Benzyl ((1R,2R,3R,4R,5R)-3-((S)-1-((tert-butyldimethylsilyl)oxy)ethyl)-5-(((tert-butyldiphenylsilyl)oxy)methyl)-3-(3,3-dimethylureido)-4-hydroxy-4-methyl-6-oxabicyclo[3.1.0]hexan-2-yl)carbamate (13)

A flame-dried 25-mL round-bottomed flask was charged with ketone 12 (1.7 g, 2.3 mmol, 1.0 equiv) and THF (23 mL). The solution was cooled to 0° C. and MeMgBr (3M in THF, 7.6 mL, 22.9 mmol, 10.0 equiv) was added dropwise. The reaction was stirred at 0° C. until TLC analysis indicated complete ketone consumption, typically 2 h. Saturated NH$_4$Cl$_{(aq.)}$ (20 mL) was carefully added dropwise and the resulting mixture was extracted with EtOAc (3×15 mL). The combined organic extracts were washed with brine (20 mL), dried with magnesium sulfate, and concentrated in vacuo. The crude product was purified via flash chromatography (90:10 to 70:30 hexanes:EtOAc) to afford carbinol 13 as a clear, viscous oil with >10:1 diastereoselection (1.3 g, 75%). The enantiomeric ratio was assayed at this intermediate and was found to be 95:5. This composition was determined by SFC analysis (Chiralcel, OD, 4.0% MeOH, 1.5 mL/min, 150 bar, 210 urn; t$_R$-minor 34.4 min, t$_R$-major 37.6 min). Analytical data: $[\alpha]_D^{19}$ +7.2 (c=0.70, CHCl$_3$); $^1$H NMR (600 MHz, CDCl$_3$): δ 7.73 (d, J=7.8 Hz, 2H), 7.70 (d, J=7.2 Hz, 2H), 7.45-7.30 (m, 12H), 5.55 (br s, 1H), 5.21 (d, J=12.6 Hz, 1H), 5.17 (br s, 1H), 5.07 (d, J=12.0 Hz, 1H), 4.77 (br s, 1H), 4.64 (dd, J=8.4, 3.6 Hz, 1H), 4.21 (d, J=12.6 Hz, 1H), 4.12 (d, J=12.6 Hz, 1H), 3.90 (s, 1H), 2.75 (s, 6H), 1.30 (s, 3H), 1.25 (d, J=6.0 Hz, 3H), 1.07 (s, 9H), 0.97 (s, 9H), 0.11 (s, 3H), −0.01 (s, 3H); $^{13}$C NMR (150 MHz, CDCl$_3$): δ 158.8, 156.5, 136.3, 135.6, 135.5, 134.7, 133.3, 132.9, 129.6, 129.4, 128.4, 128.2, 128.1, 127.7, 127.6, 127.6, 67.1, 66.8, 62.1, 58.3, 36.1, 26.7, 26.5, 25.7, 23.8, 19.6, 19.2, 17.8, −4.2, −5.5; LRMS (ESI$^+$) Calcd. for C$_{42}$H$_{61}$N$_3$O$_7$Si$_2$+H, 776.41. Found, 776.36. IR (thin film, cm$^{-1}$) 3430, 2429, 2359, 1716, 1635, 1506, 1456, 1112, 831, 700; TLC (90:10 hexanes/EtOAc): R$_f$=0.35.

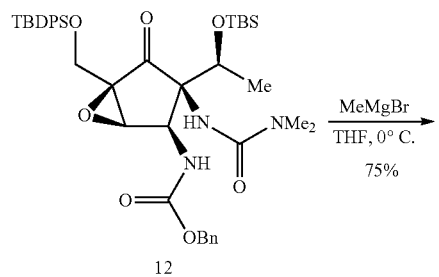

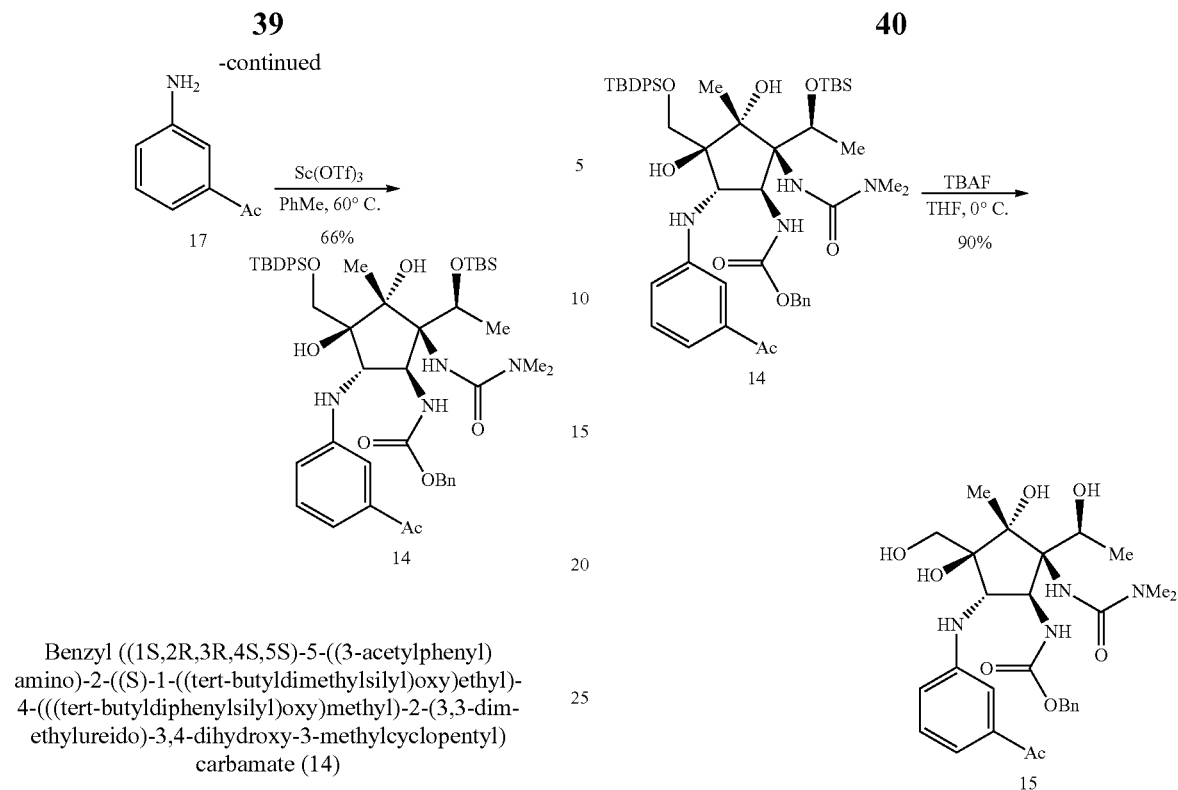

Benzyl ((1S,2R,3R,4S,5S)-5-((3-acetylphenyl)amino)-2-((S)-1-((tert-butyldimethylsilyl)oxy)ethyl)-4-(((tert-butyldiphenylsilyl)oxy)methyl)-2-(3,3-dimethylureido)-3,4-dihydroxy-3-methylcyclopentyl)carbamate (14)

In a nitrogen-filled glove box, a flame-dried 100-mL round-bottomed flask was charged with Sc(OTf)$_3$ (0.38 g, 0.77 mmol, 3.0 equiv). The flask was capped with a rubber septum and removed from the glove box. Toluene (20 mL) was added and to the resulting suspension were added aniline 17 (0.35 g, 2.6 mmol, 10.0 equiv) and a toluene solution (1.5 mL) of epoxide 13 (0.20 g, 0.26 mmol, 1.0 equiv). The reaction was heated to 60° C. with vigorous stirring and maintained for 14 h. (Note: increased reaction times led to product decomposition), The reaction was cooled to rt, diluted with H$_2$O (10 mL) and EtOAc (10 mL), and the resulting mixture was extracted with EtOAc (3×10 mL). The combined organic extracts were washed with 0.5M HCl$_{(aq.)}$ (2×20 mL), saturated NaHCO$_{3(aq.)}$ (15 mL), dried with magnesium sulfate, and concentrated in vacuo. The crude product was purified via flash chromatography (90:10 to 80:20 hexanes:EtOAc) to afford anilino-alcohol 14 as a yellow, viscous oil (0.16 g, 66%) with recovery of the unreacted epoxide 13 (0.04 g, 18%). Analytical data: $[\alpha]_D^{19}$ −39.3 (c=0.70, CHCl$_3$); $^1$H NMR (600 MHz, CDCl$_3$): δ 8.21 (d, J=6.6 Hz, 1H), 7.70 (d, J=6.6 Hz, 2H), 7.51 (d, J=7.2 Hz, 2H), 7.39 (t, J=7.2 Hz, 1H), 7.32 (t, J=7.2 Hz, 2H), 7.28-7.22 (m, 8H), 7.16 (t, J=7.2 Hz, 2H), 7.12 (t, J=7.8 Hz, 1H), 6.79 (d, J=7.8 Hz, 1H), 6.13 (s, 5.88 (s, 1H), 5.39-5.36 (m, 1H), 5.36 (s, 1H), 5.04 (d, J=12.0 Hz, 1H), 5.01 (d, J=12.0 Hz, 1H), 4.78 (dd, J=4.6, 6.6 Hz, 1H), 4.37 (d, J=10.2 Hz, 1H), 4.13 (s, 1H), 3.68 (dd, J=4.6, 3.0 Hz, 1H), 3.48 (d, J=10.8 Hz, 1H), 2.96 (s, 6H), 2.49 (s, 3H), 1.69 (s, 3H), 1.41 (d, J=6, 6 Hz, 3H), 0.98 (s, 9H), 0.92 (s, 9H), 0.12 (s, 3H), 0.02 (s, 3H); $^{13}$C NMR (150 MHz, CDCl$_3$): δ 198.7, 158.6, 158.4, 149.5, 137.7, 136.6, 135.6, 135.4, 132.4, 132.0, 129.6, 128.8, 128.2, 128.1, 127.8, 127.6, 118.2, 117.0, 112.6, 83.6, 81.0, 70.3, 68.4, 66.9, 66.5, 63.0, 59.3, 36.6, 26.7, 26.7, 25.7, 21.2, 19.4, 19.0, 17.7, −4.3, −6.1; LRMS (ESI$^+$) Calcd. for C$_{50}$H$_{70}$N$_8$Si$_2$+Na, 933.46. Found, 933.35. IR (thin film, cm$^{-1}$) 3361, 2953, 2358, 1716, 1698, 1652, 1539, 1488, 1472, 1243, 1041, 829, 701; TLC (80:20 hexanes:EtOAc): R$_f$=0.35.

Benzyl ((1S,2R,3R,4S,5S)-5-((3-acetylphenylamino)-2-(3,3-dimethylureido)-3,4-dihydroxy-2-((S)-1-hydroxyethyl)-4-(hydroxymethyl)-3-methylcyclopentyl)carbamate (15)

A 20-mL scintillation vial was charged with silyl ether 14 (0.25 g, 0.28 mmol, 1.0 equiv) and THF (5.5 mL). The resulting solution was cooled to 0° C., and TBAF (1 M solution in THF, 1.1 mL, 1.1 mmol, 4.0 equiv) was added. The reaction was allowed to stir at 0° C. until TLC analysis indicated consumption of the starting material, typically 30 min. The reaction was diluted with brine (3 mL) and EtOAc (3 mL) and extracted with EtOAc (3×7 mL). The combined organic extracts were dried with magnesium sulfate and concentrated in vacuo. The crude product was purified via flash chromatography (60:40 petroleum ether:acetone) to afford tetraol 15 as a pale yellow, viscous oil (0.14 g, 90%). Analytical data: $[\alpha]_D^{19}$+26.0 (c=0.70, CHCl$_3$); $^1$H NMR (600 MHz, CDCl$_3$): δ 7.36 (s, 4H), 7.29 (br s, 1H), 7.23 (br s, 1H), 7.12 (br s, 1H), 6.99 (d, J=7.8 Hz, 1H), 6.75 (d, J=6.6 Hz, 1H), 6.02 (d, J=7.2 Hz, 1H), 5.80 (br s, 1H), 5.48 (d, J=7.8 Hz, 1H), 5.27 (br s, 1H), 5.13 (br s, 2H), 4.14-4.10 (m, 1H), 4.06 (br s, 2H), 3.80 (br s, 2H), 3.74-3.68 (m, 1H), 3.55 (m, 1H), 2.87 (s, 6H), 2.52 (s, 3H), 1.42 (s, 3H), 1.25 (br s, 3H); $^{13}$C NMR (150 MHz, CDCl$_3$): δ 198.7, 158.7, 155.8, 146.6, 138.3, 136.0, 129.7, 128.6, 128.4, 118.4, 112.0, 88.2, 83.9, 73.2, 71.7, 67.4, 66.9, 64.2, 61.8, 61.2, 36.7, 29.7, 26.7, 22.7, 21.2, 18.0, 14.1; LRMS (ESI$^+$) Calcd. For C$_{28}$H$_{38}$N$_4$O$_8$+Na, 581.26. Found, 581.23. IR (thin film, cm$^{-1}$) 3392, 2938, 1716, 1684, 1652, 1635, 1540, 1507, 1473, 1456, 1361, 1243, 739; TLC (60:40 petroleum ether/acetone): R$_f$=0.30.

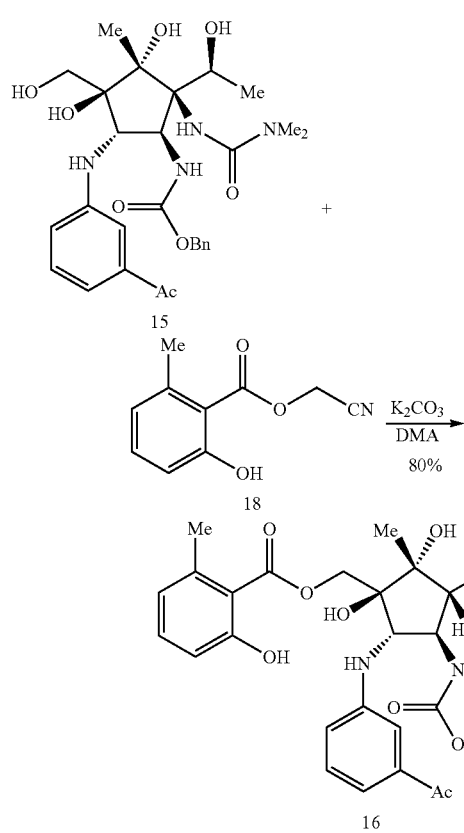

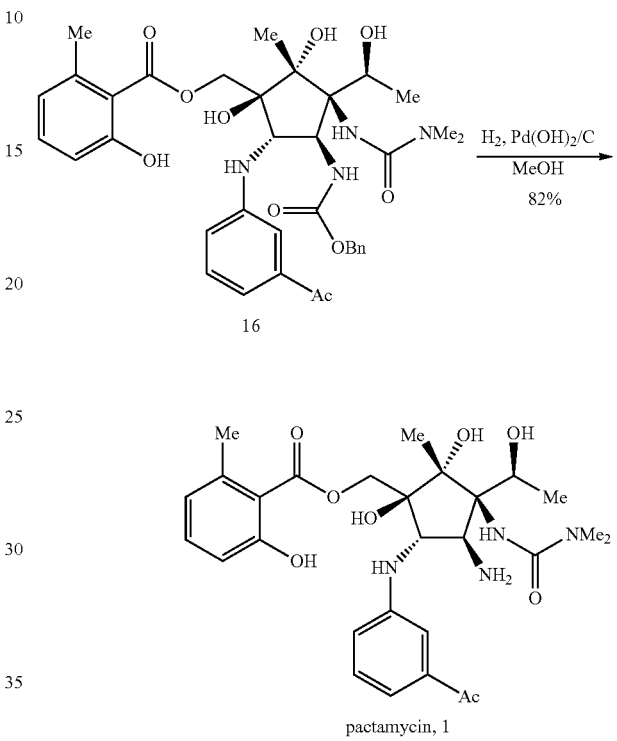

pactamycin, 1

(((1S,2R,3R,4S,5S)-5-((3-acetylphenyl)amino)-4-(((benzyloxy)carbonyl)amino)-3-(3,3-dimethylureido)-1,2-dihydroxy-3-((S)-1-hydroxyethyl)-2-methylcyclopentyl)methyl-2-hydroxy-6-methylbenzoate (16)

A flame-dried 20-mL scintillation vial was charged with cyanomethyl ester 18 (0.0075 g, 0.044 mmol, 1.1 equiv) and dimethylacetamide (DMA) (0.3 mL). $K_2CO_3$ (0.005 g, 0.04 mmol, 1.0 equiv) was added, and the resulting mixture was stirred for 1 h. The in situ generated ketene solution was transferred to a stirred solution of tetraol 15 (0.02 g, 0.04 mmol, 1.0 equiv) in DMA (0.7 mL). The reaction was stirred until TLC analysis indicated full consumption of the tetraol starting material, typically 3 h. The reaction was cooled to 0° C. and quenched by the dropwise addition of saturated $NH_4Cl_{(aq.)}$ (1.5 mL). The resulting mixture was extracted with EtOAc (3×5 mL), washed with $H_2O$ (10 ml), brine (10 mL), dried with magnesium sulfate, and concentrated in vacuo. The crude product was purified via flash chromatography (50:50 Hexanes:EtOAc) to afford an inseparable mixture of salicylate 16 (0.02 g, 80%) and an unknown impurity (15% by NMR analysis) as a pale yellow, viscous oil. Analytical data: $[\alpha]_D^{19}$+33.6 (c=0.70, $CHCl_3$); $^1H$ NMR (600 MHz, $CDCl_3$): δ 10.87 (s, 1H), 7.52 (br s, 1H), 7.36 (br s, 5H), 7.30-7.22 (m, 4H), 7.10 (s, 1H), 6.81 (d, J=8.4 Hz, 1H), 6.63 (d, J=7.2 Hz, 1H), 6.13 (s, 1H), 5.79 (d, J=9.0 Hz, 1H), 5.72 (d, J=9.6 Hz, 1H), 5.23-5.10 (m, 3H), 4.91-4.84 (m, 2H), 4.06 (br s, 2H), 3.80 (d, J=9.6 Hz, 1H), 3.69 (s, 1H), 2.85 (s, 7H), 2.30 (s, 3H), 1.42 (s, 3H), 1.26 (s, 3H); $^{13}C$ NMR (150 MHz, $CDCl_3$): δ 198.3, 173.4, 162.9, 158.5, 155.3, 146.0, 141.6, 138.3, 135.0, 129.7, 128.6, 128.5, 123.2, 119.4, 118.4, 115.8, 111.9, 111.6, 99.7, 88.6, 85.0, 73.9, 72.3, 67.5, 66.8, 66.6, 65.4, 62.7, 36.7, 23.9, 21.0, 18.0, 17.4; LRMS (ESI$^+$) Calcd. For $C_{36}H_{44}N_4O_{10}$+Na, 715.30. Found, 715.26. IR (thin film, cm$^{-1}$) 3392, 2965, 1867, 1698, 1670, 1541, 1456, 1374, 1249, 874, 737; TLC (50:50 EtOAc:Hexanes): $R_f$=0.30.

Pactamycin (1):

A 4-mL vial was charged with salicylate 16 (0.0075 g, 0.01 mmol, 1.0 equiv), and Pd(OH)$_2$/C (20 wt. %, 0.005 g). MeOH (1 mL) was added and the vial was sealed with a Teflon cap. The atmosphere was replaced by $H_2$ (balloon, ~1 atm.) and stirred until TLC analysis indicated complete consumption of the starting material, typically 20 min. The resulting suspension was filtered through a pad of CELITE® 545 (diatomaceous earth, filter aid) and washed with MeOH. The homogeneous solution was concentrated in vacuo. The crude residue was purified by flash chromatography (98:2 $CH_2Cl_2$:MeOH) affording pactamycin (0.005 g, 82%) as a pale yellow solid. Analytical data: $[\alpha]_D^{19}$+27.4 (c=0.40, $CHCl_3$); $^1H$ NMR (600 MHz, $CDCl_3$): δ 10.98 Or s, 1H), 7.91 (d, J=10.8 Hz, 1H), 7.26-7.23 (m, 4H), 7.18-7.16 (m, 2H), 6.81-6.78 (m, 2H), 6.64 (d, J=7.2 Hz, 1H), 5.78 (br s, 1H), 5.67 (d, J=10.8 Hz, 1H), 4.84 and 4.79 (ABq, J=12.6 Hz, 2H), 3.93 (m, 1H), 3.80 (d, J=10.2 Hz, 1H), 2.99 (s, 6H), 2.95 (s, 1H), 2.55 (s, 3H), 2.38 (s, 3H), 1.55 (s, 3H), 1.04 (d, J=6.0 Hz, 3H); $^{13}C$ NMR (150 MHz, $CDCl_3$): δ 198.5, 172.6, 162.8, 159.2, 146.6, 141.2, 138.3, 134.6, 129.6, 123.0, 118.7, 118.4, 115.7, 112.0, 110.8, 88.8, 84.9, 74.3, 71.5, 68.7, 65.4, 63.2, 36.9, 29.7, 26.7, 24.1, 21.1, 18.1; HRMS (ESI$^1$) Calcd. for $C_{28}H_{38}N_4O_8$+H, 559.2762. Found, 559.2763. IR (thin film, cm$^{-1}$) 3393, 2938, 2359, 2341, 1698, 1652, 1520, 1473, 1418, 1338, 873, 668; TLC (95:5 $CH_2Cl_2$/MeOH): $R_f$=0.30.

Preparation of Crystalline Derivative S4

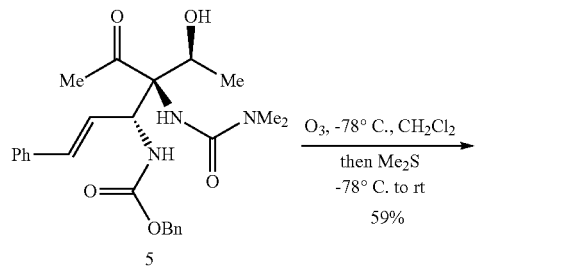

Benzyl ((3S,4R,5S)-4-acetyl-4-(3,3-dimethylureido)-2-hydroxy-5-methyl-tetrahydrofuran-3-yl)carbamate (S3)

A 250-mL round-bottomed flask was charged with alcohol 5 (1.4 g, 3.1 mmol, 1.0 equiv) and $CH_2Cl_2$ (62 mL). The resulting solution was cooled to −78° C., and a stream of $O_3$ was bubbled through the solution until a blue color was observed, typically 5 min. The mixture was sparged with $O_2$ for 5 min, and $Me_2S$ (0.9 mL, 12.4 mmol, 4.0 equiv) was added. The resulting mixture was warmed to rt and stirred for 12 h and concentrated in vacuo. Flash chromatography (60:40 EtOAc:Hexanes) afforded an inseparable ~5:1 diastereomeric mixture of lactols (S3) (0.69 g, 58%) as a viscous oil. Analytical data: $[\alpha]_D^{19}$+18.3 (c=1.00, $CHCl_3$); $^1H$ NMR (600 MHz, $CDCl_3$): δ 8.08 (d, J=12.0 Hz, 1H), 7.37-7.28 (m, 5H), 6.15 (br s, 1H), 5.53 (dd, J=6.0, 6.6 Hz, 1H), 5.39 (d, J=8.4 Hz, 1H), 5.10 (d, J=12.6 Hz, 1H), 4.98 (d, J=12.6 Hz, 1H), 4.70 (q, J=7.2 Hz, 1H), 4.63 (dd, J=6.0, 3.0 Hz, 1H), 2.83 (s, 1H), 2.80 (s, 6H), 238 (s, 3H), 1.17 (d, J=6.6 Hz, 3H); $^{13}C$ NMR (150 MHz, $CDCl_3$): δ 204.6, 157.0, 156.2, 136.1, 128.4, 128.1, 127.9, 95.9, 71.4, 66.7, 59.3, 36.0, 26.6, 14.1; LRMS ($ESI^+$) Calcd. for $C_{18}H_{25}N_3O_6$+H, 380.18. Found, 380.17. IR (thin film, $cm^{-1}$) 3390, 2938, 2066, 1700, 1636, 1522, 1351, 1230, 1063, 752; TLC (60:40 EtOAc:Hexanes): $R_f$=0.35.

(3S4R,5S)-4-acetyl-3-(((benzyloxy)carbonyl)amino)-4-(3,3-dimethylureido)-5-methyl-tetrahydrofuran-2-yl-4-nitrobenzoate (S4)

A flame-dried, 50-mL round-bottomed flask was charged with diastereomeric lactols (S3) (0.69 g, 1.8 mmol, 1.0 equiv) and $CH_2Cl_2$ (18 mL). The resulting solution was cooled to 0° C. and $NEt_3$ (0.76 mL, 5.4 mmol, 3.0 equiv), DMAP (0.02 g, 0.18 mmol, 0.1 equiv), and 4-nitrobenzoyl chloride (0.51 g, 2.7 mmol, 1.5 equiv) were added sequentially. The reaction was stirred at 0° C. until TLC analysis indicated complete consumption of the lactol, typically 30 min. Water (10 mL) was added to the reaction and the resulting mixture was extracted with $CH_2Cl_2$ (3×10 mL). The combined organic extracts were dried with magnesium sulfate and concentrated in vacuo. The crude residue was purified by flash chromatography (30:70 Hexanes:EtOAc) affording a ~5:1 diastereomeric mixture of 4-nitrobenzoate S4 (0.71 g, 74%) as a yellow powder. Slow evaporation (MeOH) at room temperature afforded crystals suitable for X-ray analysis. (Note: to obtain analytically pure S4, a small portion of the fractions were collected from column chromatography, resulting in a discrepancy in the diastereomeric ratio.) Analytical data: $[\alpha]_D^{19}$−11.8 (c=1.00, $CHCl_3$); $^1H$ NMR (600 MHz, $CDCl_3$): δ 8.42 (d, J=9.0 Hz, 2H), 8.27 (d, J=9.0 Hz, 2H), 7.31-7.24 (m, 5H), 6.82 (d, J=6.0 Hz, 1H), 6.66 (d, J=9.0 Hz, 1H), 5.94 (br s, 1H), 5.13 (q, J=6.6 Hz, 1H), 5.06 (d, J=12.0 Hz, 1H), 5.02 (d, J=16.2 Hz, 1H), 4.99 (m, 1H), 2.90 (s, 6H), 2.38 (s, 3H), 1.17 (d, J=6.6 Hz, 3H); $^{13}C$ NMR (150 MHz, $CDCl_3$): δ 203.8, 163.5, 157.4, 156.6, 150.6, 136.1, 135.0, 131.2, 128.4, 128.3, 128.1, 127.9, 123.5, 95.4, 72.5, 66.7, 57.9, 36.2, 26.4, 14.4; LRMS ($ESI^+$) Calcd. for $C_{25}H_{28}N_4O_9$+H, 529.19. Found, 529.20. IR (thin film, $cm^{-1}$) 3393, 3113, 2944, 1715, 1637, 1526, 1349, 1271, 1081, 1011, 736; TLC (70:30 EtOAc:Hexanes): $R_f$=0.30.

REFERENCES

1. Y.-W. Chin, M. J. Balanus, H. B. Chai, A. D. Kinghorn, *AAPS J.* 8, E239 (2006).
2. F. von Nussbaum, M. Brands, B. Hinzen, S. Weigand, D. Habich, *Angew. Chem. Int. Ed.* 45, 5072 (2006).
3. C. Drahl, B. F. Cravatt, E. J. Sorensen, *Angew. Chem. Int. Ed.* 44, 5788 (2005).
4. K. Nakanishi, in *Comprehensive Natural Products Chemistry*, D. Barton, K. Nakanishi, O. Meth-Cohn, U. Sankawa, Eds. (Elsevier, New York, 1999), vol. 1, pp. 23.
5. A. D. Argoudelis, H. K. Jahnke, J. A. Fox, *Antimicrob. Agents. Chemother.* 191 (1962).
6. G. Dinos, D. N. Wilson, Y. Teraoka, W. Szaflarski, P, Fucini, D. Kalpaxis, K. H. Nierhaus, *Mol. Cell* 13, 113 (2004).
7. D. D. Weller, A. Haber, K. L. Rinehart Jr., P. F. Wiley, *J. Antibiot.* 31, 997 (1978).

8. P. F. Wiley, H. K. Jahnke, F. MacKellar, R. B. Kelly, A. D. Argoudelis, *J. Org. Chem.* 35, 1420 (1970).
9. D. J. Duchamp, Abstracts, American Crystallographic Association Winter Meeting, Albuquerque, N. Mex., 23 (1972).
10. D. E. Brodersen, W. M. Clemons, A. P. Carter, R. J. Morgan-Warren, B. T. Wimberly, V. Ramakrishnan, *Cell* 103, 1143 (2000).
11. M. Iwatsuki, et al. *J. Antibiot.* 65, 169 (2012).
12. W. Lu, N. Roongsawang, T. Mahmud, *Chem. Biol.* 18, 425 (2011).
13. K. Otoguro, M. Iwatsuki, A. Ishiyama, M. Namatame, A. Nishihara-Tukashima, S. Shibahara, S. Kondo, H. Yamada, S. Omura, *J. Antiobiot.* 63, 381 (2010).
14. K. Dobashi, K. Isshiki, T. Sawa, T. Obata, M. Hamada, H. Naganawa, T. Takita, T. Takeuchi, H. Urnezawa, *J. Antiobiot.* 39, 1779 (1986).
15. S. Hanessian, R. R. Vakiti, S. Dorich, S. Banerjee, F. Lecomte, J. R. Del Valle, J. Zhang, B. Deschenes-Simard, *Angew. Chem., Int. Ed.* 50, 3497 (2011).
16. S. Hanessian, R. R. Vakiti, A. Dorich, S. Banerjee, B. Deschenes-Simard, *J. Org. Chem.* 77, 9458 (2012).
17. T. Tsujimoto, T. Nishikawa, D. Urabe, M. Isobe, *Synlett* 433 (2005).
18. S. Knapp, Y. Yu, *Org. Lett.* 9, 1359 (2007).
19. J. T. Malinowski, S. J. McCarver, J. S. Johnson, *Org. Lett.* 14, 2878 (2012).
20. T. J. Haussener, R. E. Looper, *Org. Lett.* 14, 3632 (2012).
21. N. Matsumoto, T. Tsujimoto, A. Nakazaki, M. Isobe, T. Nishikawa, *RSC Adv.* 2, 9448 (2012).
22. S. Lou, B. M. Taoka, A. Ting, S. E. Schaus, *J. Am. Chem. Soc.* 127, 11256 (2005).
23. A. Ting, S. Lou, S. E. Schaus, *Org. Lett.* 8, 2003 (2006).
24. Y. Li, J.-P. Feng, W.-H. Wang, J. Chen, X.-P. Cao, *J. Org. Chem.* 72, 2344 (2007).
25. B. M. Trost, C. D. Haffner, D. J. Jebaratnam, M. J. Krische, A. P. Thomas, *J. Am. Chem. Soc,* 121, 6183 (1999).
26. J. M. J. Verlaak, A. J. H. Klunder, B. Zwanenburg, *Tetrahedron Lett.* 23, 5463 (1982).
27. L. Shi, K. Meyer, M. F. Greaney, *Angew. Chem. Int. Ed.* 49, 9250 (2010).
28. P. Serrano, A. Liebaria, A. Delgado, *J. Org. Chem.* 67, 7165 (2002).
29. W. M. Pearlman, *Tetrahedron Lett.* 8, 1663 (1967).

The foregoing is illustrative of the present invention, and is not to be construed as limiting thereof. The invention is defined by the following claims, with equivalents of the claims to be included therein.

That which is claimed is:

1. A compound of Formula IX:

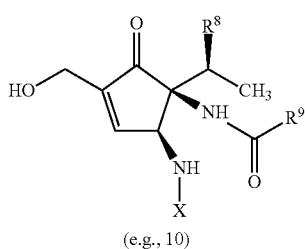

(e.g., 10)

wherein:
$R^8$ is H, hydroxy, silyloxy, acyloxy, or alkoxy; and
$R^9$ is —$N(R^cR^d)$, —$OR^c$, or —$SR^c$, where $R^c$ and $R^d$ are each independently selected alkyl, aryl, or heteroaryl, or $R^c$ and $R^d$ together form an alkylene bridge; and
X is a protecting group.

2. A method of making a compound of Formula IX:

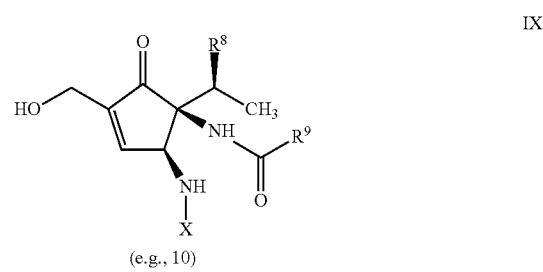

(e.g., 10)

wherein:
$R^8$ is H, hydroxy, silyloxy, acyloxy, or alkoxy; and
$R^9$ is —$N(R^cR^d)$, —$OR^c$, or —$SR^c$, where $R^c$ and $R^d$ are each independently selected alkyl, aryl, or heteroaryl, or $R^c$ and $R^d$ together form an alkylene bridge; and
X is a protecting group;
said method comprising condensing a compound of Formula X:

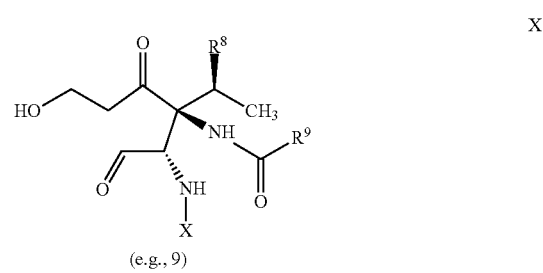

(e.g., 9)

in an aldol condensation reaction to produce said compound of Formula IX.

3. A compound of Formula X:

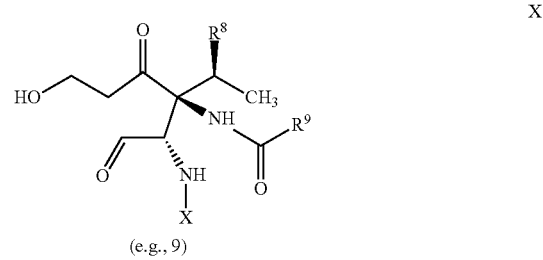

(e.g., 9)

wherein:
$R^8$ is H, hydroxy, silyloxy, acyloxy, or alkoxy; and
$R^9$ is —$N(R^cR^d)$, —$OR^c$, or —$SR^c$, where $R^c$ and $R^d$ are each independently selected alkyl, aryl, or heteroaryl, or $R^c$ and $R^d$ together form an alkylene bridge; and
X is a protecting group.

* * * * *